US012788743B2

(12) United States Patent
Michaelson et al.

(10) Patent No.: US 12,788,743 B2
(45) Date of Patent: Nov. 10, 2026

(54) ACTIVATORS OF THE LIPIDATING TRANSPORTER ATP BINDING CASSETTE PROTEIN TYPE 1 (AB-CA1) AND THERAPEUTIC USES THEREOF

(71) Applicant: RAMOT AT TEL-AVIV UNIVERSITY LTD., Tel Aviv (IL)

(72) Inventors: Daniel Michaelson, Tel Aviv (IL); Zvi Menachem, Tel Aviv (IL); Abraham Nudelman, Rehovot (IL)

(73) Assignee: RAMOT AT TEL-AVIV UNIVERSITY LTD., Tel-Aviv (IL)

( * ) Notice: Subject to any disclaimer, the term of this patent is extended or adjusted under 35 U.S.C. 154(b) by 994 days.

(21) Appl. No.: 17/759,928

(22) PCT Filed: Feb. 1, 2021

(86) PCT No.: PCT/IL2021/050114
§ 371 (c)(1),
(2) Date: Aug. 2, 2022

(87) PCT Pub. No.: WO2021/152601
PCT Pub. Date: Aug. 5, 2021

(65) Prior Publication Data
US 2023/0103965 A1 Apr. 6, 2023

Related U.S. Application Data

(60) Provisional application No. 62/969,093, filed on Feb. 2, 2020.

(51) Int. Cl.
*A61K 31/4245* (2006.01)
*A61K 31/454* (2006.01)
*A61K 31/496* (2006.01)
*A61K 31/5377* (2006.01)
*A61K 31/55* (2006.01)
*A61P 25/28* (2006.01)

(52) U.S. Cl.
CPC ........ *A61K 31/4245* (2013.01); *A61K 31/454* (2013.01); *A61K 31/496* (2013.01); *A61K 31/5377* (2013.01); *A61K 31/55* (2013.01); *A61P 25/28* (2018.01)

(58) Field of Classification Search
CPC .............. A61K 31/4245; A61K 31/454; A61K 31/496; A61K 31/5377; A61K 31/55; A61P 25/28
See application file for complete search history.

(56) References Cited

U.S. PATENT DOCUMENTS

| | | | | |
|---|---|---|---|---|
| 10,512,667 | B2 | 12/2019 | Kerppola | |
| 2005/0282818 | A1 | 12/2005 | Ramesh | |
| 2014/0296307 | A1* | 10/2014 | Fletcher | C07D 271/12 548/126 |

FOREIGN PATENT DOCUMENTS

| | | | |
|---|---|---|---|
| WO | 2006002284 | A1 | 1/2006 |
| WO | 2008124838 | A1 | 10/2008 |
| WO | 2012032018 | A1 | 3/2012 |

OTHER PUBLICATIONS

Jacobo-Albavera et al., The Role of the ATP-Binding Cassette A1 (ABCA1) in Human Disease Int. J. Mol. Sci. 2021, 22, 1593. (Year: 2021).*

Alder-Baerens et al., (2005) Headgroup-specific exposure of phospholipids in ABCA1-expressing cells. J Biol Chem 280(28): 26321-26329.

Apostolova et al., (2018) Associations of the Top 20 Alzheimer Disease Risk Variants With Brain Amyloidosis. JAMA Neurol 75(3): 328-341.

Babashamsi et al., (2019) ABCA1 and metabolic syndrome; a review of the ABCA1 role in HDL-VLDL production, Insulin-glucose homeostasis, inflammation and obesity. Diabetes Metab Syndr 13(2): 1529-1534.

Bar-El, Ben-Moshe, Menachem Michaelson (2022) ApoE4: An Emerging Therapeutic Target for Alzheimer's Disease. AD/PD™ 2022, Advances in Science & Therapy. International Conference on Alzheimer's and Parkinson's Diseases and related neurological disorders. Mar. 15-20, 2022, Barcelona, Spain. Abstract.

Belton et al., (1976) Anticancer agent—XI. Antitumour activity of 4-amino-7-nitrobenzofuroxans and related compounds. Proc R Ir Acad B 76(9): 133-149.

Boehm-Cagan and Michaelson (2014) Reversal of apoE4-driven brain pathology and behavioral deficits by pexarotene. J Neurosci 34(21): 7293-7301.

Boehm-Cagan et al., (2016) ABCA1 Agonist Reverses the ApoE4-Driven Cognitive and Brain Pathologies. J Alzheimers Dis 54(3): 1219-1233.

Boehm-Cagan et al., (2016) Differential Effects of apoE4 and Activation of ABCA1 on Brain and Plasma Lipoproteins. PLoS One 11(11): e0166195.

Buchwald et al., (1980) Long-term, continuous intravenous heparin administration by an implantable infusion pump in ambulatory patients with recurrent venous thrombosis. Surgery 88(4): 507-516.

Calderón-Garcidueñas et al., (2017) Apolipoprotein E4, Gender, Body Mass Index, Inflammation, Insulin Resistance, and Air Pollution Interactions: Recipe for Alzheimer's Disease Development in Mexico City Young Females. J Alzheimers Dis 58(3): 613-630.

Chan et al., (2018) Differential Binding of Human ApoE Isoforms to Insulin Receptor is Associated with Aberrant Insulin Signaling in AD Brain Samples. NeuroMolecular Medicine 20: 124-132.

Chapman et al., (2001) APOE genotype is a major predictor of long-term progression of disability in MS. Neurology 56(3): 312-316.

Corder et al., (1993) Gene dose of apolipoprotein E type 4 allele and the risk of Alzheimer's disease in late onset families. Science 261(5123): 921-923.

(Continued)

*Primary Examiner* — Adam C Milligan
*Assistant Examiner* — William Y Lee
(74) *Attorney, Agent, or Firm* — Ballard Spahr LLP

(57) ABSTRACT

The present invention relates to compounds that are functional activators of ATP binding cassette protein type 1 (AB-CA1), and their use for treating diseases and conditions implicating ABCA1, including Alzheimer's Disease (AD) and atherosclerosis.

16 Claims, 13 Drawing Sheets

(56) References Cited

OTHER PUBLICATIONS

Farfara et al., (2011) γ-Secretase component presenilin is important for microglia β-amyloid clearance. Ann Neurol 69(1): 170-180.
Frisardi (2012) Apolipoprotein E genotype: the innocent bystander or active bridge between metabolic syndrome and cognitive impairment? J Alzheimers Dis 30 Suppl 2: S283-S304.
Giacobini and Gold (2013) Alzheimer disease therapy-moving from amyloid-β to tau. Nat Rev Neurol 9(12): 677-686.
Götz and Ittner (2008) Animal models of Alzheimer's disease and frontotemporal dementia. Nat Rev Neurosci 9(7): 532-544.
Hu et al., (2015) Opposing effects of viral mediated brain expression of apolipoprotein E2 (apoE2) and apoE4 on apoE ipidation and AB metabolism in apoE4-targeted replacement mice. Mol Neurodegener 10: 6.
Kassam et al., (2016) Association of the APOE-ϵ4 allele with outcome of traumatic brain injury in children and youth: a meta-analysis and meta-regression. Published Online First; Published in final edited form as: J Neurol Neurosurg Psychiatry 87(4): 433-440.
Koldamova et al., (2010) The role of ATP-binding cassette transporter A1 in Alzheimer's disease and neurodegeneration. Biochim Biophys Acta. Author manuscript; available in PMC Jul. 16, 2013. Published in final edited form as: Biochim Biophys Acta. Aug. 2010; 1801(8): 824-830.
Kolovou et al., (2006) Tangier disease four decades of research: a reflection of the importance of HDL. Curr Med Chem 13(7): 771-782.
Larramona-Arcas et al., (2020) Sex-dependent calcium hyperactivity due to lysosomal-related dysfunction in astrocytes from APOE4 versus APOE3 gene targeted replacement mice. Mol Neurodegener 15(1): 35.
Li et al., (2015) The Association Between Apolipoprotein E and Functional Outcome After Traumatic Brain Injury: A Meta-Analysis. Medicine (Baltimore) 94(46): e2028.
Liu et al., (2012) Apolipoprotein E gene polymorphism in a Chinese population with vascular dementia: a meta-analysis. Dement Geriatr Cogn Disord 33(2-3): 96-103.
Mehta et al., (2017) Why do trials for Alzheimer's disease drugs keep failing? A discontinued drug perspective for 2010-2015. Expert Opin Investig Drugs. Author manuscript; available in PMC Jun. 1, 2018. Published in final edited form as: Expert Opin Investig Drugs. Jun. 2017; 26(6): 735-739.
Morikawa et al., (2005) Production and characterization of astrocyte-derived human apolipoprotein E isoforms from Immortalized astrocytes and their interactions with amyloid-beta. Neurobiol Dis 19(1-2): 66-76.
Qian et al., (2017) Structure of the Human Lipid Exporter ABCA1. Cell 169(7): 1228-1239.e10.
Rannikmäe et al., (2014) APOE associations with severe CAA-associated vasculopathic changes: collaborative meta-analysis. J Neurol Neurosurg Psychiatry 85(3): 300-305.
Rawat et al., (2019) ApoE4 Alters ABCA1 Membrane Trafficking in Astrocytes. J Neurosci 39(48): 9611-9622.
Robbins et al., (2020) Dysregulation of Insulin-Linked Metabolic Pathways in Alzheimer's Disease: Co-Factor Role of Apolipoprotein E ϵ4. J Alzheimers Dis Rep 4(1): 479-493.
Roses (1996) Apolipoprotein E alleles as risk factors in Alzheimer's disease. Annu Rev Med 47: 387-400.
Safieh et al., (2019) ApoE4: an emerging therapeutic target for Alzheimer's disease. BMC Med 17(1): 64.
Sankaranarayanan et al., (2011) A sensitive assay for ABCA1-mediated cholesterol efflux using BODIPY-cholesterol. J Lipid Res 52(12): 2332-2340.
Saudek et al., (1989) A preliminary trial of the programmable implantable medication system for insulin delivery. N Engl J Med 321(9): 574-579.
Saunders et al., (1993) Association of apolipoprotein E allele epsilon 4 with late-onset familial and sporadic Alzheimer's disease. Neurology 43(8): 1467-1472.
Schneider et al., (2014) Clinical trials and late-stage drug development for Alzheimer's disease: an appraisal from 1984 to 2014. J Intern Med 275(3): 251-283.
Shi et al., (2017) ApoE4 markedly exacerbates tau-mediated neurodegeneration in a mouse model of tauopathy. Nature. Author manuscript; available in PMC Sep. 28, 2018. Published in final edited form as: Nature. Sep. 28, 2017; 549 (7673): 523-527.
Shin et al., (2014) Apolipoprotein E mediation of neuro-inflammation in a murine model of multiple sclerosis. J Neuroimmunol. Author manuscript; available in PMC Jun. 15, 2015. Published in final edited form as: J Neuroimmunol. Jun. 15, 2014; 271(0): 8-17.
Simonovitch et al., (2016) Impaired Autophagy in APOE4 Astrocytes. J Alzheimers Dis 51(3): 915-927.
Tensaouti et al., (2020) Apolipoprotein E regulates the maturation of injury-induced adult-born hippocampal neurons following traumatic brain injury. PLoS One 15(3): e0229240.
Treves et al., (1996) APOE-ϵ4 in patients with Alzheimer disease and vascular dementia. Alzheimer Dis Assoc Disord 10(4): 189-191.
Tsuang et al., (2013) APOE ϵ4 increases risk for dementia in pure synucleinopathies. JAMA Neurol 70(2): 223-228.
Westerterp et al., (2014) ATP-binding cassette transporters, atherosclerosis, and inflammation. Circ Res 114(1): 157-170.
Wyss-Coray et al., (2003) Adult mouse astrocytes degrade amyloid-beta in vitro and in situ. Nat Med 9(4): 453-457.
Yassine et al., (2016) ABCA1-Mediated Cholesterol Efflux Capacity to Cerebrospinal Fluid is Reduced in Patients With Mild Cognitive Impairment and Alzheimer's Disease. J Am Heart Assoc 5(2): e002886.

* cited by examiner

ACTIVATORS OF THE LIPIDATING TRANSPORTER ATP BINDING CASSETTE PROTEIN TYPE 1 (AB-CA1) AND THERAPEUTIC USES THEREOF

FIELD OF THE INVENTION

The present invention relates to compounds that are functional activators of ATP binding cassette protein type 1 (ABCA1), and their use for treating diseases and conditions involving ABCA1, including Alzheimer's Disease (AD) and atherosclerosis, by administering a functional activator of ATP binding cassette protein type 1 (ABCA1).

BACKGROUND OF THE INVENTION

Many disorders of brain function lead to cognitive decline, among which Alzheimer's disease (AD) is considered the most prevalent. The definition of AD itself is not simple. Unique among human diseases, the accepted definition requires a combination of clinical manifestations (i.e., dementia) and structural changes, namely deposition of amyloid β (Aβ) and hyperphosphorylated tau tangles (neurofibrillary tangles) in the brain. Since various other brain disorders can lead to cognitive deterioration comparable to that observed in AD and, similarly, identical pathological changes can occur in people who do not manifest cognitive decline, diagnoses of AD require both specific cognitive deterioration and neuropathological changes. It is therefore not surprising that attempts to focus treatment on deposits have so been disappointing [1-3]. The classical approach to this issue focuses on AD pathology and on a rare genetic form of early onset autosomal dominant AD, as beacons. Unfortunately, this approach, which focuses on the Aβ and tau pathological hallmarks of AD, did not yield clinically significant results [4].

Epidemiologic studies exploring the risk factors for AD elucidated a large number of genetic associations, the most important of which is the apolipoprotein E gene on chromosome 17 (APOE gene, apoE protein) [5]. ApoE is the major brain lipoprotein and is expressed as three common forms that differ from each other by one or two amino acids, termed apoE2, apoE3, and apoE4, of which apoE4 is the most prevalent genetic risk factor for AD [6-8]. More than half of AD patients carry at least one apoE4 allele, which reduces the age of onset of the disease in a gene dose-dependent manner by as much as 7 to 9 years per allele copy [6]. Recent AD and corresponding animal model studies revealed that apoE4 is hypo-lipidated relative to its AD benign isoform apoE3 [9-13]. Furthermore, the present inventors have shown that reversal of the hypo-lipidation of apoE4 in mice by treatment with either an activator of gene expression of the main brain lipidating protein, ABCA1, or with an agonistic peptide of ABCA1 reverses the apoE4-driven brain pathology [11, 13]. The ABCA1 agonist with which these results were obtained is a 36-mer peptide and its therapeutic application is therefore limited due to challenges in administration and limited bioavailability.

Additionally, it has been shown that increasing the expression of ABCA1 by activating the ABCA1 promotor with a retinoid X receptor (RXR)-liver X receptor (LXR) ligand bexarotene, results in increased expression of ABCA1. However, activation of the LXR/RXR system affects a large number of additional genes and is thus not specific to ABCA1 [12].

Additional diseases for which apoE4 is a risk factor include atherosclerosis and inflammation [19], Cerebral Amyloid Angiopathy (CAA) [20], Dementia with Lewy Bodies (DLB) [21], tauopathy [22], cerebrovascular disease [23], multiple sclerosis [24], vascular dementia [23], poor outcome following head injury [25], and metabolic syndrome and glucose homeostasis [26, 28]. Diseases associated with ABCA1 include Tangier disease (both homozygotes and heterozygotes) [27]. Alzheimer's Disease (AD) is the main cause of dementia of the elderly. The classical approach to this issue, which focuses on the Aβ and tau pathological hallmarks of AD, did not yield clinically significant results. There is an urgent an unmet need in the art for new and alternative therapeutic approaches.

SUMMARY OF THE INVENTION

The present invention relates to the discovery of low molecular weight and brain permeable ABCA1 functional activators that are useful in treating diseases and conditions involving ABCA1. In some embodiments, the compounds reverse hypo-lipidation of apoE4 and, consequently, are useful for treating diseases and conditions in which apoE4 has been implicated as a risk factor. In particular embodiments, the compounds of the invention are useful in treating Alzheimer's Disease (AD), or in reducing and/or delaying the onset of cognitive impairment associated with AD. In other embodiments, the compounds of the invention are useful in treating atherosclerosis.

As contemplated herein, the objects of the present invention have been achieved by performing the following sequential steps: 1) Phenotypic High-Throughput Screening (HTS) utilizing a cellular cholesterol translocation activation assay; 2) Assessments by an orthogonal assay of the extents to which the HTS hits obtained in Step 1 can reverse the apoE4 driven impaired digestion of senile plaques, 3) Cytotoxicity measurements of the hits identified in Step 2; 4) Target recognition experiments in which the binding of the hits to ABCA1 is determined; 5) hit expansion/optimization and generation of leading compounds utilizing medicinal chemistry and X-ray crystallography of the extra cellular domain of ABCA1; and 6) preparation of new compounds, which are derivative of some of the identified leading compounds.

Steps 1 to 4 yielded 5 compounds which bind to the extracellular domain of ABCA1; score positively by the cholesterol translocation and the orthogonal assays and are not toxic. Two more such compounds were identified by a hit expansion medicinal chemistry approach, leading to seven compounds (Table 1). As contemplated herein, these compounds and analogs represented by general Formulae (I), (I-a), (II), (IIa), (IIb), (III), (IV) and (V) are effective at treating diseases and conditions in which ABCA1 is implicated. Step 6 yielded additional 5 such compounds.

According to some embodiments, there is provided a pharmaceutical composition comprising a functional activator of ATP binding cassette protein type 1 (ABCA1) of a pharmaceutical grade and a pharmaceutically acceptable carrier or excipient, wherein the functional activator of ABCA1 is a compound represented by the structure of formula (I-a):

(I-a)

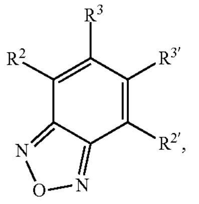

wherein $R^2$ is selected from the group consisting of nitro ($NO_2$) and —NRR'; $R^{2'}$ is selected from the group consisting of H, halogen, amino ($NH_2$), and —NRR'; R and R' are each independently H, ($C_1$-$C_6$)-alkyl, or an aryl, or R and R' together with the nitrogen to which they are attached form a heterocyclic ring; and wherein each of said alkyl, cycloalkyl, heterocyclyl, aryl and heteroaryl is optionally substituted by a halogen, an alkyl, a hydroxyalkyl or a haloalkyl; and $R^3$ and $R^{3'}$ are each independently selected from the group consisting of H, —X—$(CH_2)_t$-G and halogen; X is O, S or NH; G is $CO_2H$, OH or $CO_2$—$C_{1-4}$ alkyl; t is selected from the group consisting of 0, 1, 2, 3, 4, 5 and 6; and salts and solvates thereof.

According to some embodiments, $R^2$ is nitro. According to some embodiments, $R^{3'}$ is H. According to some embodiments, $R^2$ is nitro and $R^{3'}$ is H. According to some embodiments, $R^2$ is NRR'. According to some embodiments, $R^3$ is H. According to some embodiments, $R^{2'}$ is NRR' and R; is H. According to some embodiments, at least one of $R^3$ and $R^{3'}$ is H.

According to some embodiments, the compound is selected from the group consisting of Compound C, Compound F, Compound G, Compound H, Compound J, Compound K, Compound L, Compound Q, Compound R, Compound S, Compound T, Compound U, and salts and solvates thereof, the structures thereof are detailed herein. Each possibility represents a separate embodiment. According to some embodiments, the compound is selected from the group consisting of Compound C, Compound H, Compound J, Compound Q, Compound R, Compound S, Compound T, Compound U, and salts and solvates thereof. According to some embodiments, the compound is Compound C, a salt or a solvate thereof. Each possibility represents a separate embodiment. According to some embodiments, the compound is Compound H, a salt or a solvate thereof.

According to some embodiments, the compound directly increases the enzymatic activity of ABCA1. According to some embodiments, activation of ABCA1 increases efflux of cholesterol.

According to some embodiments, the present invention provides a pharmaceutical composition comprising a functional activator of ATP binding cassette protein type 1 (ABCA1) and a pharmaceutically acceptable carrier or excipient, wherein the functional activator of ABCA1 is a compound represented by the structure of formula (I):

(I)

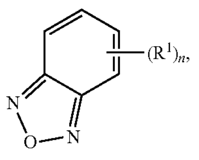

wherein $R^1$ is selected from the group consisting of halogen, nitro ($NO_2$), ($C_1$-$C_6$)-alkyl, $C_2$-$C_8$ alkenyl, $C_2$-$C_8$ alkynyl, cycloalkyl, aryl, heterocyclyl, heteroaryl, ($C_1$-$C_6$)-alkylaryl, ($C_1$-$C_6$)-alkylcycloalkyl, ($C_1$-$C_6$)-alkylheterocyclyl, ($C_1$-$C_6$)-alkylheteroaryl, haloalkyl, hydroxy (OH), ($C_1$-$C_6$)-alkyloxy, aryloxy, thio (SH), ($C_1$-$C_6$)-alkylthio, arylthio, —C(O)R, —C(O)OR, —X—$(CH_2)_t$-G, amino ($NH_2$), —NRR', —C(O)NRR', —S(O)NRR' and —$S(O)_2$NRR'; R and R' are each independently H, ($C_1$-$C_6$)-alkyl, or an aryl, or R and R' together with the nitrogen to which they are attached form a heterocyclic ring; and wherein each of said alkyl, cycloalkyl, heterocyclyl, aryl and heteroaryl is optionally substituted by a halogen, an alkyl, a hydroxyalkyl or a haloalkyl; X is a bond, O, S or NH; G is selected from the group consisting of: $CO_2H$, OH, halogen, $CO_2$—$C_{1-4}$ alkyl, thiocarboxylic acid, dithiocarboxylic acid, sulfonic acid, sulfinic acid, phosphonic acid, and phosphate, an amine, an alkylamine and an arylamine; t is selected from the group consisting of 0, 1, 2, 3, 4, 5 and 6; n is selected from the group consisting of 1, 2, 3 and 4; and salts and solvates thereof, for use in the treatment of disease or condition related to ATP binding, wherein the disease or condition is selected from the group consisting of Alzheimer's Disease (AD), atherosclerosis, inflammation, Cerebral amyloid angiopathy (CAA), dementia with Lewy Bodies, taupathy, cerebrovascular disease, multiple sclerosis, vascular dementia, traumatic head injury, metabolic syndrome, glucose homeostasis and Tangier disease (TD).

According to some embodiments, the present invention provides a functional activator of ATP binding cassette protein type 1, as detailed herein for use in the treatment of disease or condition related to ATP binding. According to some embodiments, the present invention provides a compound as detailed herein for use in the treatment of disease or condition related to ATP binding.

According to some embodiments, the compound is of a pharmaceutical grade purity. According to some embodiments, n is 2. According to some embodiments, the functional activator of ABCA1 is a compound of Formula (I), represented by the structure of formula (I-a), as shown herein, wherein $R^2$ is selected from the group consisting of nitro ($NO_2$) and —NRR'; $R^{2'}$ is selected from the group consisting of H, halogen, amino ($NH_2$), and —NRR'; R and R' are each independently H, ($C_1$-$C_6$)-alkyl, or an aryl, or R and R' together with the nitrogen to which they are attached form a heterocyclic ring; and wherein each of said alkyl, cycloalkyl, heterocyclyl, aryl and heteroaryl is optionally substituted by a halogen, an alkyl, a hydroxyalkyl or a haloalkyl; and $R^3$ and $R^{3'}$ are each independently selected from the group consisting of H, —X—$(CH_2)_t$-G and halogen; X is O, S or NH; G is $CO_2H$, OH or $CO_2$—$C_{1-4}$ alkyl, t is selected from the group consisting of 0, 1, 2, 3, 4, 5 and 6; and salts and solvates thereof. According to some embodiments, $R^2$ is nitro. According to some embodiments, $R^{2'}$ is NRR'. According to some embodiments, $R^3$, $R^{3'}$ or each one of $R^3$, and $R^{3'}$ is H. According to some embodiments, the compound is selected from the group consisting of Compound C, Compound F, Compound G, Compound H, Compound J, Compound K, Compound L, Compound Q, Compound R, Compound S, Compound T, Compound U, and salts and solvates thereof. Each possibility represents a separate embodiment. According to some embodiments, the compound is selected from the group consisting of Compound C, Compound H, Compound J, Compound Q. Compound R, Compound S, Compound T, Compound U, and salts and solvates thereof. Each possibility represents a separate embodiment. According to some embodiments, the compound is Compound C, a salt or a solvate thereof. According to some embodiments, the compound is Compound H, a salt or a solvate thereof. According to some embodiments, the compound directly increases the enzymatic activity of ABCA1. According to some embodiments, activation of ABCA1 increases efflux of cholesterol. According to some embodiments, the disease or condition is Alzheimer's Disease (AD).

According to some embodiments, the present invention provides a compound represented by the structure of formula (I-a), as described herein, wherein $R^2$ is nitro ($NO_2$); $R^2$ is —NRR'; R and R' together with the nitrogen to which they are attached form a heterocyclic ring, wherein the heterocyclic ring is substituted by at least one $C_{1-4}$ alkyl, and wherein each of said $C_{1-4}$ alkyl and heterocyclic ring is optionally substituted by a halogen; $R^3$ and $R^{3'}$ are each independently selected from the group consisting of H, $C_{1-4}$ alkyl, COOH, COO—$C_{1-4}$ alkyl and halogen; and salts and solvates thereof. According to some embodiments, each of $R^3$ and $R^{3'}$ is H. According to some embodiments, the heterocyclic ring is selected from the group consisting of methylpiperidine and methylpyrrolidine. According to some embodiments, the compound is Compound S, a salt or a solvate thereof. According to some embodiments, the compound is Compound T, a salt or a solvate thereof. According to some embodiments, the compound is Compound U, a salt or a solvate thereof.

According to some embodiments, the present invention provides a method for treating a disease or condition related to ATP binding cassette protein type 1 (ABCA1), the method comprising the step of administering to a subject in need thereof a functional activator of ABCA1, wherein the functional activator of ABCA1 is a compound represented by the structure of formula (I) as detailed herein. According to some embodiments, the disease or condition is Alzheimer's Disease (AD).

According to further embodiments, the present invention relates to a method of treating a disease or condition implicating ATP binding cassette protein type 1 (ABCA1), by administering to a subject in need thereof a non-peptidic compound which is a functional activator of ABCA1. In some embodiments, the compound directly increases the enzymatic activity of ABCA1. In some embodiments, the compound is brain permeable.

In some embodiments, the disease or condition is characterized by hypo-lipidation of apolipoprotein E4 (apoE4). In accordance with this embodiment, activation of ABCA1 increases lipidation of apolipoprotein E4 (apoE4). In other embodiments, activation of ABCA1 increases efflux of cholesterol. In particular embodiments, the disease or condition is selected from the group consisting of Alzheimer's Disease (AD), atherosclerosis, inflammation, Cerebral amyloid angiopathy (CAA), dementia with Lewy Bodies, taupathy, cerebrovascular disease, multiple sclerosis, vascular dementia, traumatic head injury, metabolic syndrome, glucose homeostasis and Tangier Disease (TD). In one specific embodiment, the disease or condition is Alzheimer's Disease (AD). Thus, in one embodiment, the present invention relates to a method of treating Alzheimer's Disease (AD), the method comprising the step of administering to a subject in need thereof a non-peptidic compound which functions as an activator of ABCA1 or a composition comprising said compound. In another specific embodiment, the disease or condition is atherosclerosis.

Thus, in one embodiment, the present invention relates to a method of treating atherosclerosis, the method comprising the step of administering to a subject in need thereof a non-peptidic compound which functions as an activator of ABCA1 or a composition comprising said compound.

In other embodiments, the present invention relates to a method for treating a disease or condition involving hypo-lipidated apolipoprotein E4 (apoE4), the method comprising the step of administering to a subject in need thereof a non-peptidic compound which is a functional activator of ATP binding cassette protein type 1 (ABCA1), wherein activation of ABCA1 increases lipidation of apolipoprotein E4 (apoE4), thereby treating said disease or condition. In other embodiments, the present invention relates to a method for treating Alzheimer's Disease (AD), comprising the step of administering to a subject in need thereof a non-peptidic compound which is a functional activator of ATP binding cassette protein type 1 (ABCA1), wherein activation of ABCA1 increases lipidation of apolipoprotein E4 (apoE4), thereby treating AD. In some embodiments, apoE4 is hypo-lipidated in the subject.

In other embodiments, the present invention relates to a non-peptidic compound which is a functional activator of ATP binding cassette protein type 1 (ABCA1), for use in treating a disease or condition involving ABCA1. In some embodiments, the disease or condition implicates hypolipidated apolipoprotein E4 (apoE4). In one particular embodiment, the disease is Alzheimer's Disease (AD), wherein activation of ABCA1 results in lipidation of apolipoprotein E4 (apoE4), thereby treating of AD. In another embodiment, the disease is atherosclerosis. In some embodiments, the compounds of the invention are useful in treating Alzheimer's Disease (AD). In particular embodiments, treating AD comprises attenuating or reversing the pathology of AD by reducing accumulation of amyloid β (Aβ) and/or hyperphosphorylated tau tangles, reversing synaptic impairment, improving cognitive function, or any combination thereof. Each possibility represents a separate embodiment of the present invention.

In other aspects, the present invention relates to increasing lipidation of hypo-lipidated apolipoprotein E4 (apoE4), comprising the step of contacting the apoE4 with an ATP binding cassette protein type 1 (ABCA1) in the presence of a non-peptidic compound which is a functional activator of ABCA1. "Contacting" may be conducted in-vitro, for example in cell culture, or in-vivo.

In some embodiments, the non-peptidic compound is represented by the structure of formula (I). In other embodiments, the compound is represented by the structure of formula (I-a). In other embodiments, the compound is represented by the structure of formula (IIa). In other embodiments, the compound is represented by the structure of formula (IIb). In other embodiments, the compound is represented by the structure of formula (III). In other embodiments, the compound is represented by the structure of formula (IV). In other embodiments, the compound is represented by the structure of formula (V). In some embodiments, the compound is represented by any of the structures of Compounds (A), (B), (C), (D), (E), (F), (G), (H), (J), (K), (L), (M), (N), (O), and (P). Each possibility represents a separate embodiment. The structures of these compounds are provided in the detailed description hereinbelow.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PRESENT INVENTION

Figure 1:
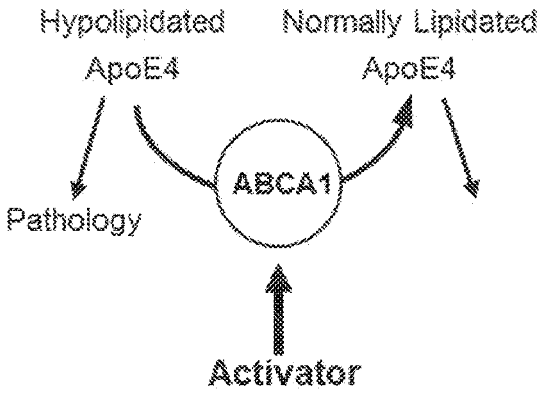
FIG. 1: Schematic representation of reversal of hypolipidation of ApoE4.

The present invention relates to the discovery of low molecular weight and brain permeable ABCA1 functional activators that can reverse the hypo-lipidation of apoE4 and consequently, are useful in treating diseases and conditions that involve ABCA1 and/or implicate hypolipidated apoE4.

As contemplated herein, the present invention relates to compounds represented by the structure of formulae (I), (I-a), (IIa), (IIb), (III), (IV) and (V), which are ABCA1 functional activators and therefore useful for treating diseases and conditions that involve ABCA1 and/or implicate hypolipidated apoE4 including, but not limited to, Alzheimer's Disease and atherosclerosis. The present invention further relates to pharmaceutical compositions comprising compounds represented by the structure of formulae (I) and (I-a) and uses thereof for treatment of such conditions. In addition, the present invention relates to new compounds, which were not previously disclosed as detailed herein.

Formula (I-a)

Thus, according to some embodiments, the present invention provides a pharmaceutical composition comprising a functional activator of ATP binding cassette protein type 1 (ABCA1) and a pharmaceutically acceptable carrier or excipient, wherein the functional activator of ABCA1 is a compound represented by the structure of formula (I-a):

(I-a)

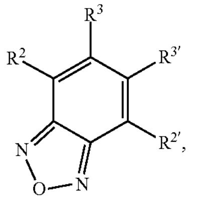

wherein $R^2$ is selected from the group consisting of nitro ($NO_2$) and —NRR';

$R^{2'}$ is selected from the group consisting of H, halogen, amino ($NH_2$), and —NRR';

R and R' are each independently H, ($C_1$-$C_6$)-alkyl, or an aryl, or R and R' together with the nitrogen to which they are attached form a heterocyclic ring; and wherein each of said alkyl, cycloalkyl, heterocyclyl, aryl and heteroaryl is optionally substituted by a halogen, an alkyl, a hydroxyalkyl or a haloalkyl; and $R^3$ and $R^{3'}$ are each independently selected from the group consisting of H, —X—$(CH_2)_t$-G and halogen;

X is O, S or NH;

G is $CO_2H$, OH or $CO_2$—$C_{1-4}$ alkyl;

t is selected from the group consisting of 0, 1, 2, 3, 4, 5 and 6;

and salts and solvates thereof.

According to some embodiments, the functional activator of ABCA1 is provided at a pharmaceutical grade. According to some embodiments, the functional activator of ABCA1 is provided at a purity of at least 96%. According to some embodiments, the functional activator of ABCA1 is provided at a purity of at least 97%. According to some embodiments, the functional activator of ABCA1 is provided at a purity of at least 98%. According to some embodiments, the functional activator of ABCA1 is provided at a purity of at least 99%. According to some embodiments, the functional activator of ABCA1 is provided at a purity of at least 99.5%. According to some embodiments, the functional activator of ABCA1 is provided at a purity of at least 99.8%. According to some embodiments, the functional activator of ABCA1 is provided at a purity of at least 99.9%.

The term "pharmaceutical grade" has its standard meaning of being suitable for use in pharmaceutical products. Thus, the term "pharmaceutical grade" means sufficient quality and efficacy to meet the introductory requirements of the applicable U.S. Pharmacopoeia (USP) and the European Pharmacopoeia (Ph Eur).

The term "pharmaceutically acceptable" is defined as being suitable for administration to humans without adverse events. Thus, the term "pharmaceutically acceptable" means approved by a regulatory agency of the Federal or a state government or listed in the U.S. Pharmacopeia or other generally recognized pharmacopeia for use in animals and, more particularly, in humans.

As discussed herein, the compounds of the present invention are brain permeable and low molecular weight, according to some embodiments. Thus, according to some embodiments, the functional activator of ABCA1 is a compound having a molecular weight of no more than 600 gr/mol. According to some embodiments, the functional activator of ABCA1 is a compound having a molecular weight of no more than 550 gr/mol. According to some embodiments, the functional activator of ABCA1 is a compound having a molecular weight of no more than 500 gr/mol. According to some embodiments, the functional activator of ABCA1 is a compound having a molecular weight of no more than 450 gr/mol. According to some embodiments, the functional activator of ABCA1 is a compound having a molecular weight of no more than 400 gr/mol. According to some embodiments, the functional activator of ABCA1 is a compound having a molecular weight of no more than 375 gr/mol. According to some embodiments, the functional activator of ABCA1 is a compound having a molecular weight of no more than 350 gr/mol. According to some embodiments, the functional activator of ABCA1 is a compound having a molecular weight of no more than 325 gr/mol. According to some embodiments, the functional activator of ABCA1 is a compound having a molecular weight of no more than 300 gr/mol.

According to some embodiments, $R^2$ is nitro.

According to some embodiments, $R^{2'}$ is selected from the group consisting of H, halogen, and —NRR'. According to some embodiments, $R^{2'}$ is selected from the group consisting of halogen and —NRR'. According to some embodiments, $R^2$ is —NRR'.

According to some embodiments, R and R' are each independently H, ($C_1$-$C_4$)-alkyl, or an aryl, or R and R' together with the nitrogen to which they are attached form a heterocyclic ring. According to some embodiments, R and R' are each independently ($C_1$-$C_4$)-alkyl, or R and R' together with the nitrogen to which they are attached form a heterocyclic ring. According to some embodiments, R and R' are each independently ($C_1$-$C_4$)-alkyl. According to some embodiments, Rand R' are each independently ($C_1$-$C_2$)-alkyl. According to some embodiments, R and R' are each independently methyl. According to some embodiments, each one of the ($C_1$-$C_2$)-alkyl, ($C_1$-$C_4$)-alkyl, ($C_{1-6}$)-alkyl and methyl as disclosed herein is optionally substituted by at least one halogen. According to some embodiments, each one of said alkyls in unsubstituted. According to some embodiments, R is $CH_3$. According to some embodiments, R' is $CH_3$. According to some embodiments, each one of R' and R is $CH_3$.

According to some embodiments, R and R' together with the nitrogen to which they are attached form a heterocyclic ring. According to some embodiments, the heterocyclic ring is selected from the group consisting of a three membered heterocyclic ring, a four membered heterocyclic ring, a five membered heterocyclic ring, a six membered heterocyclic ring, a seven membered heterocyclic ring and an eight membered heterocyclic ring. According to some embodiments, the heterocyclic ring is selected from the group consisting of a five membered heterocyclic ring, a six membered heterocyclic ring and a seven membered heterocyclic ring. According to some embodiments, the heterocyclic ring is a non-aromatic heterocycle. According to some embodiments, the heterocyclic ring is selected from the group consisting of piperidine, morpholine, piperazine, azepane and pyrrolidine. According to some embodiments, each of said heterocycles is optionally substituted by a halogen, an alkyl, a hydroxyalkyl or a haloalkyl. According to some embodiments, the heterocyclic ring is selected from the group consisting of methylpiperidine, unsubstituted piperidine, N-(2-hydroxyethyl)-piperazine, N-methipiperazine, unsubstituted morpholine, unsubstituted azepane, methylpyrrolidine, and unsubstituted pyrrolidine.

According to some embodiments, $R^{2'}$ is a halogen. According to some embodiments, the halogen is selected from chlorine, fluorine and bromine. According to some embodiments, the halogen is selected from chlorine and fluorine. According to some embodiments, the halogen is chlorine.

According to some embodiments, at least one of $R^{3'}$ and $R^3$ is H. According to some embodiments, $R^3$ is H. According to some embodiments, $R^3$ is H. According to some embodiments, each one of $R^{3'}$ and $R^3$ is H. According to some embodiments, one of $R^{3'}$ and $R^3$ is H and the other one of $R^3$ and $R^{3'}$ is $—X—(CH_2)_t$-G. According to some embodiments, $R^3$ is H and $R^{3'}$ is $—X—(CH_2)_t$-G. According to some embodiments, $R^{3'}$ is $—X—(CH_2)_t$-G. According to some embodiments, X is S or O. According to some embodiments, X is S.

According to some embodiments, G is $CO_2H$, or $CO_2$—$C_{1-4}$ alkyl. According to some embodiments, G is $CO_2H$.

According to some embodiments, the compound is selected from the group consisting of:

Compound C

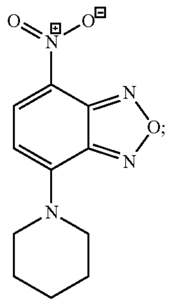

Compound F

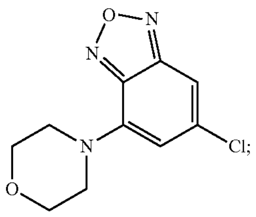

Compound G

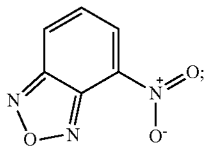

-continued

Compound H

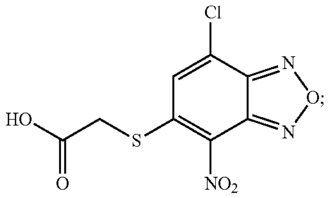

Compound J

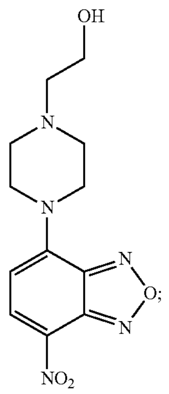

Compound K

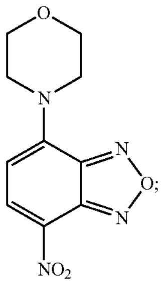

Compound L

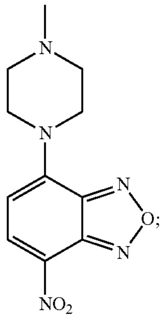

Compound Q

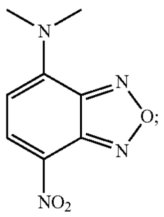

Compound R

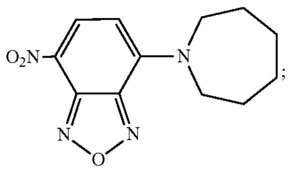

-continued

Compound S

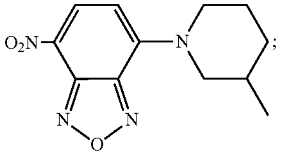

Compound T

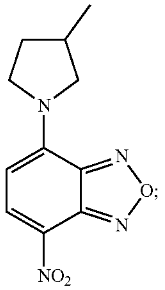

Compound U

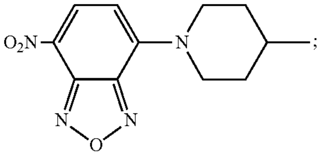

and salts and solvates thereof.

According to some embodiments, the compound is selected from the group consisting of Compound C, Compound H, Compound J, Compound K, Compound Q, Compound R, Compound S, Compound T, Compound U, and salts and solvates thereof.

Each possibility represents a separate embodiment. According to some embodiments, the compound is selected from the group consisting of Compound C, Compound H, Compound J, Compound Q, Compound R, Compound S, Compound T, Compound U, and salts and solvates thereof. According to some embodiments, the compound is selected from the group consisting of Compound C, Compound H, and salts and solvates thereof.

According to some embodiments, the compound is Compound C, a salt or a solvate thereof. According to some embodiments, the compound is Compound F, a salt or a solvate thereof. According to some embodiments, the compound is Compound G, a salt or a solvate thereof. According to some embodiments, the compound is Compound H, a salt or a solvate thereof. According to some embodiments, the compound is Compound J, a salt or a solvate thereof. According to some embodiments, the compound is Compound K, a salt or a solvate thereof. According to some embodiments, the compound is Compound L, a salt or a solvate thereof. According to some embodiments, the compound is Compound Q, a salt or a solvate thereof. According to some embodiments, the compound is Compound R, a salt or a solvate thereof. According to some embodiments, the compound is Compound S, a salt or a solvate thereof. According to some embodiments, the compound is Compound T, a salt or a solvate thereof. According to some embodiments, the compound is Compound U, a salt or a solvate thereof Chemical Definitions An "alkyl" group refers to any saturated aliphatic hydrocarbon, including straight-chain and branched-chain alkyl groups. The alkyl group may be unsubstituted or substituted by one or more groups selected from halogen, hydroxy, hydroxyalkyl, haloalkyl, alkoxyalkyl, alkoxy, carbonyl, amido, alkylamido, dialkylamido, nitro, amino, alkylamino, dialkylamino, carboxy, thio and thioalkyl.

An "alkenyl" group refers to an aliphatic hydrocarbon group containing at least one carbon-carbon double bond including straight-chain, branched-chain and cyclic alkenyl groups. The alkenyl group can be unsubstituted or substituted through available carbon atoms with one or more groups defined hereinabove for alkyl.

An "alkynyl" group refers to an aliphatic hydrocarbon group containing at least one carbon-carbon triple bond including straight-chain and branched-chain. The alkynyl group can be unsubstituted or substituted through available carbon atoms with one or more groups defined hereinabove for alkyl.

The term "cycloalkyl" used herein alone or as part of another group refers to any saturated or unsaturated (e.g., cycloalkenyl, cycloalkynyl) monocyclic or polycyclic group.

The cycloalkyl group can be unsubstituted or substituted with any one or more of the substituents defined above for alkyl.

The term "aryl" used herein alone or as part of another group refers to an aromatic ring system containing from 6-14 ring carbon atoms. The aryl ring can be a monocyclic, bicyclic, tricyclic and the like. The aryl group can be unsubstituted or substituted through available carbon atoms with one or more groups defined hereinabove for alkyl.

The term "heteroaryl" used herein alone or as part of another group refers to a heteroaromatic system containing at least one heteroatom ring wherein the atom is selected from nitrogen, sulfur and oxygen. If nitrogen is a ring atom, the present invention also contemplates the N-oxides of the nitrogen containing heteroaryls. The heteroaryl group can be unsubstituted or substituted through available atoms with one or more groups defined hereinabove for alkyl.

The term "heterocyclic ring" or "heterocyclyl" used herein alone or as part of another group refers to a rings that have 1 to 4 heteroatoms. The heterocyclyl group can be unsubstituted or substituted through available atoms with one or more groups defined hereinabove for alkyl.

The term "halogen" or "halo" as used herein alone or as part of another group refers to chlorine, bromine, fluorine, and iodine. The term "haloalkyl" refers to an alkyl group having some or all of the hydrogens independently replaced by at least one halogen.

One or more of the compounds of the invention, may be present as a salt. According to some embodiments, the salt is a pharmaceutically acceptable salt. It is to be understood that salt of compound of the present invention may include acidic or basic salts. For example, many of the compounds of the present invention include a basic hydrogen atom, which may be protonated upon contacting with an acid to form a salt. Suitable acids include, but are not limited to hydrochloric acid, hydrobromic acid, phosphoric acid and sulfuric acid.

The term "salt" encompasses both basic and acid addition salts, including but not limited to, carboxylate salts or salts with amine nitrogens, and include salts formed with the organic and inorganic anions and cations discussed below. Furthermore, the term includes salts that form by standard acid-base reactions with basic groups (such as amino groups) and organic or inorganic acids. Such acids include hydrochloric, hydrofluoric, trifluoroacetic, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicylic, methanesulfonic, benzenesulfonic, sorbic, picric, benzoic, cinnamic, and like acids. Each possibility represents a separate embodiment of the invention.

The term "organic or inorganic cation" refers to counter-ions for the anion of a salt. The counter-ions include, but are not limited to, alkali and alkaline earth metals (such as lithium, sodium, potassium, barium, aluminum and calcium); ammonium and mono-, di- and tri-alkyl amines such as trimethylamine, cyclohexylamine; and the organic cations, such as dibenzylammonium, benzylammonium, 2-hydroxyethylammonium, bis(2-hydroxyethyl)ammonium, phenylethylbenzylammonium, dibenzylethylenediammonium, and like cations.

The present invention also includes solvates of the compounds of the present invention and salts thereof. "Solvate" means a physical association of a compound of the invention with one or more solvent molecules. This physical association involves varying degrees of ionic and covalent bonding, including hydrogen bonding. In certain instances the solvate will be capable of isolation. "Solvate" encompasses both solution-phase and isolatable solvates. Non-limiting examples of suitable solvates include ethanolates, methanolates and the like. "Hydrate" is a solvate wherein the solvent molecule is water. According to some embodiments, the solvate is a hydrate.

The novel compounds disclosed herein can be synthesized according to methods known in the art. For example, to obtain Compound T, NBD chloride (see structure below) can be reacted with an 3-methylpyrrolidine hydrochloride at room temperature in the presence of dichloroethane (DCM) and triethylamine ($NET_3$) according to the following scheme:

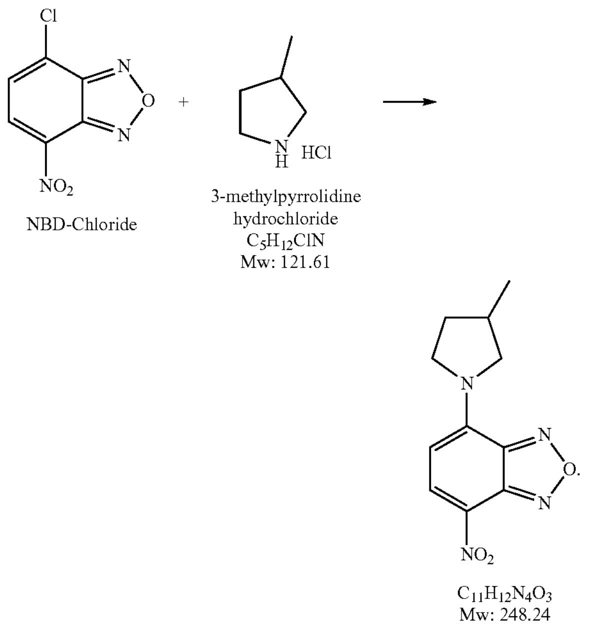

NBD-Chloride 3-methylpyrrolidine hydrochloride $C_5H_{12}ClN$ Mw: 121.61

$C_{11}H_{12}N_4O_3$ Mw: 248.24

Likewise, Compounds S and U can be prepared by reacting NBD chloride with 3-methylpiperidine and 4-methylpiperidine, respectively, at room temperature in the presence of DCM and $NET_3$. The crude compounds can be isolated and further purified, if necessary, using any suitable technique, for example, by crystallization, distillation under reduced pressure or through column chromatography. Each possibility represents a separate embodiment. The obtained compounds can be analyzed for its structure by known methods including, but not limited to, NMR and Mass spectrometry.

Formulations

The pharmaceutical compositions of the present invention can be formulated for administration by a variety of routes including oral, rectal, transdermal, parenteral (subcutaneous, intraperitoneal, intravenous, intra-arterial, transdermal and intramuscular), topical, intranasal, or via a suppository. Each possibility represents a separate embodiment of the present invention. Such compositions are prepared in a manner well known in the pharmaceutical art and comprise as an active ingredient at least one compound of the present invention as described hereinabove, and a pharmaceutically acceptable excipient or a carrier.

During the preparation of the pharmaceutical compositions according to the present invention the active ingredient is usually mixed with a carrier or excipient, which may be a solid, semi-solid, or liquid material. The compositions can be in the form of tablets, pills, capsules, pellets, granules, powders, lozenges, sachets, cachets, elixirs, suspensions, dispersions, emulsions, solutions, syrups, aerosols (as a solid or in a liquid medium), ointments containing, for example, up to 50% by weight of the active compound, soft and hard gelatin capsules, suppositories, sterile injectable solutions, and sterile packaged powders. Each possibility represents a separate embodiment of the present invention.

The carriers may be any of those conventionally used and are limited only by chemical-physical considerations, such as solubility and lack of reactivity with the compound of the invention, and by the route of administration. The choice of carrier will be determined by the particular method used to administer the pharmaceutical composition. Some examples of suitable carriers include lactose, glucose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water and methylcellulose. Each possibility represents a separate embodiment of the present invention. The formulations can additionally include lubricating agents such as talc, magnesium stearate, and mineral oil; wetting agents, surfactants, emulsifying and suspending agents; preserving agents such as methyl- and propylhydroxybenzoates; sweetening agents; flavoring agents, colorants, buffering agents (e.g., acetates, citrates or phosphates), disintegrating agents, moistening agents, anti-bacterial agents, anti-oxidants (e.g., ascorbic acid or sodium bisulfite), chelating agents (e.g., ethylenediaminetetraacetic acid), and agents for the adjustment of tonicity such as sodium chloride. Other pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerin, propylene glycol or other synthetic solvents. Water is a preferred carrier when the pharmaceutical composition is administered intravenously. Saline solutions and aqueous dextrose and glycerol solutions can also be employed as liquid carriers, particularly for injectable solutions. Each possibility represents a separate embodiment of the present invention.

For preparing solid compositions such as tablets, the principal active ingredient(s) is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing, for example, from about 0.1 mg to about 2000 mg, from about 0.1 mg to about 500 mg, from about 1 mg to about 100 mg, from about 100 mg to about 250 mg, etc. of the active ingredient(s) of the present invention.

Any method can be used to prepare the pharmaceutical compositions. Solid dosage forms can be prepared by wet granulation, dry granulation, direct compression and the like. The solid dosage forms of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate. Each possibility represents a separate embodiment of the present invention.

The liquid forms in which the compositions of the present invention may be incorporated, for administration orally or by injection, include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles. Each possibility represents a separate embodiment of the present invention.

Compositions for inhalation or insulation include solutions and suspensions in pharmaceutically acceptable aqueous or organic solvents, or mixtures thereof, and powders. The liquid or solid compositions may contain suitable pharmaceutically acceptable excipients as described above. In one embodiment, the compositions are administered by the oral or nasal respiratory route for local or systemic effect. Compositions in pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, orally or nasally, from devices that deliver the formulation in an appropriate manner.

Another formulation suitable for the compositions and methods of the present invention employs transdermal delivery devices (patches). Such transdermal patches may be used to provide continuous or discontinuous infusion of the compounds of the present invention in controlled amounts. The construction and use of transdermal patches for the delivery of pharmaceutical agents is well known in the art.

In yet another embodiment, the composition is prepared for topical administration, e.g. as an ointment, a gel a drop or a cream. For topical administration to body surfaces using, for example, creams, gels, drops, ointments and the like, the compounds of the present invention can be prepared and applied in a physiologically acceptable diluent with or without a pharmaceutical carrier. The present invention may be used topically or transdermally. Adjuvants for topical or gel base forms may include, for example, sodium carboxymethylcellulose, polyacrylates, polyoxyethylene-polyoxypropylene-block polymers, polyethylene glycol and wood wax alcohols. Each possibility represents a separate embodiment of the present invention.

Alternative formulations include nasal sprays, liposomal formulations, slow-release formulations, pumps delivering the drugs into the body (including mechanical or osmotic pumps) controlled-release formulations and the like, as are known in the art.

The compositions are preferably formulated in a unit dosage form. The term "unit dosage forms" refers to physically discrete units suitable as unitary dosages for human subjects and other mammals, each unit containing a predetermined quantity of active material(s) calculated to produce the desired therapeutic effect, in association with a suitable pharmaceutical excipient.

In preparing a formulation, it may be necessary to mill the active ingredient to provide the appropriate particle size prior to combining with the other inactive ingredients. If the active compound is substantially insoluble, it ordinarily is milled to a particle size of less than 200 mesh. If the active ingredient is substantially water soluble, the particle size is normally adjusted by milling to provide a substantially uniform distribution in the formulation, e.g. about 40 mesh.

The compounds may also be administered by any convenient route, for example by infusion or bolus injection, by absorption through epithelial linings (e.g., oral mucosa, rectal and intestinal mucosa, etc.), and may be administered together with other therapeutically active agents. The administration may be localized or it may be systemic. In addition, it may be desirable to introduce the pharmaceutical compositions of the invention into the central nervous system by any suitable route, including intra-ventricular and intrathecal injection; intra-ventricular injection may be facilitated by an intra-ventricular catheter, for example, attached to a reservoir. Pulmonary administration can also be employed, e.g., by use of an inhaler or nebulizer, and formulation with an aerosolizing agent.

A compound of the present invention can be delivered in an immediate release or in a controlled release system. In one embodiment, an infusion pump may be used to administer a compound of the invention. In one embodiment, a compound of the invention is administered in combination with a biodegradable, biocompatible polymeric implant, which releases the compound over a controlled period of time at a selected site. Examples of polymeric materials include, but are not limited to, polyanhydrides, polyorthoesters, polyglycolic acid, polylactic acid, polyethylene vinyl acetate, copolymers and blends thereof.

Furthermore, at times, the pharmaceutical compositions may be formulated for parenteral administration (subcutaneous, intravenous, intra-arterial, transdermal, intraperitoneal or intramuscular injection) and may include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that include suspending agents, solubilizers, thickening agents, stabilizers, and preservatives. Oils such as petroleum, animal, vegetable, or synthetic oils and soaps such as fatty alkali metal, ammonium, and triethanolamine salts, and suitable detergents may also be used for parenteral administration. Further, in order to minimize or eliminate irritation at the site of injection, the compositions may contain one or more nonionic surfactants. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described and known in the art. Each possibility represents a separate embodiment of the present invention.

Therapeutic Uses

As contemplated herein, the compounds and pharmaceutical compositions of the invention are functional activators of ABCA1, and are therefore useful in treating diseases or conditions in which ABCA1 and/or apoE4 are implicated, e.g., diseases and conditions connected with low activity of ABCA1. Generally, such diseases and conditions fall into two categories: 1) diseases involving ABCA1 where hypolipidation of apoE4 has been implicated as a risk factor; and 2) diseases where increased ABCA1 has generally been relevant to improved outcome, independent of apoE4.

1) Diseases Implicating ABCA1 where apoE4 has been Implicated as a Risk Factor

Without wishing to be bound to any particular hypothesis or mechanism of action, it is contemplated that ApoE4 is hypolipidated in diseases in which apoE4 is a risk factor due to either one or both of two complimentary mechanisms: (a) apoE4 is a poor substrate for ABCA1 as compared to the benign isoform apoE3; and (2) ApoE4 induces a decrease in the levels of ABCA1. The pathological consequence of either or both of these mechanisms can be counteracted by increasing the activity of ABCA1 by the compounds of the present invention.

Alzheimer's Disease

Alzheimer's Disease (AD), the main cause of dementia in elderly, currently cannot be treated effectively. Failures of AD related clinical trials may in part be due to the fact that they focus on the entire AD population as a homogeneous entity and on the assumption that Aβ metabolism plays a pivotal causative and ubiquitous role in the pathology of all of the AD patients. The present invention focuses instead on apoE4, which is expressed in more than half of the AD patients, and is expected to have a large and significant therapeutic effect.

The term "Alzheimer's Disease" includes early-onset AD (EOAD) or late-onset AD (LOAD), with each possibility representing a separate embodiment of the present invention. ApoE, which is the brain's most prevalent lipoprotein, is associated with cholesterol and phospholipids as high-density lipoprotein-like particles that play a key role in the distribution and recycling of lipids in the brain. This led to investigations of the possibility that lipids play an important role in mediating the pathological effects of apoE4. Measurement of the brain and CSF levels of docosahexaenoic acid (DHA), an essential ω-3 fatty acid critical for neuronal and brain function, revealed that DHA levels are reduced in AD patients and in apoE4 carriers. Further studies revealed that apoE4 is associated with disruption of the BBB and with phospholipid and cholesterol dysregulation. The important role of cholesterol in a variety of cellular mechanisms and its pronounced effects on Aβ levels and related mechanisms suggest that cholesterol is an important player in the pathogenesis of AD. Mouse model studies revealed that a high cholesterol diet accentuates the pathological effects of apoE4 in targeted replacement mice that express human apoE isoforms and no mouse apoE. Analysis of the degree of lipidation of the different apoE isoforms in human CSF and in the brains of apoE-targeted replacement mice revealed that, in both human and mice, apoE4 is hypolipidated relative to apoE3, and that brain apoE2 is the most lipidated isoform. The lipidation of apoE in the brain is driven by the ATP binding cassette proteins ABCA1 and ABCG1, wherein the former drives the initial lipidation of apoE, which is then further lipidated by ABCG1. Down-regulation and deletion of ABCA1 reduce the levels of plasma and brain apoE and are associated with the formation of smaller apoE-containing lipoprotein particles and with the accentuation of the apoE4 phenotype.

The finding that ABCA1 plays a major role in the lipidation of apoE and that apoE4 is hypolipidated led to the suggestion that the pathological effects of apoE4 are related to its extent of lipidation and that it may be possible to counteract the pathological effects of apoE4 by increasing ABCA1 activity. The expression of ABCA1 is regulated by LXR/RXR and can be activated in vivo by treatment with drugs such as bexarotene and 9-cis retinoic acid. Treatment of apoE4 and apoE3 mice with these agents elevates the levels of ABCA1 in both groups. This was associated with a specific increase in the lipidation of brain apoE4 but with no effect on the lipidation of apoE3. Additional studies utilizing apoE3 and apoE4 mice revealed that enhancing the expression of ABCA1 is associated with reversal of key apoE4 phenotypes such as the accumulation of Aβ and hyperphosphorylated tau in hippocampal neurons as well as neuronal and synaptic impairments and cognitive deficits.

Furthermore, the present inventors have shown that reversal of the hypo-lipidation of apoE4 in mice by treatment with either an activator of gene expression of the main brain lipidating protein, ABCA1, or with an agonistic peptide of ABCA1, both reverse the apoE4-driven brain pathology. The ABCA1 agonist with which these proof-of-principle results were obtained is a 36-mer peptide and its therapeutic application is therefore limited [12]. The present invention addresses the deficiencies in the art by discovery of low molecular weight and brain permeable ABCA1 functional activators that can reverse the hypo-lipidation of apoE4 and consequently, the associated brain pathological and cognitive effects associated with AD (FIG. 1).

Thus, in one embodiment, the present invention relates to a method for treating Alzheimer's Disease (AD), comprising the step of administering to a subject in need thereof a compound which is a functional activator of ATP binding cassette protein type 1 (ABCA1), wherein activation of ABCA1 results in lipidation of apolipoprotein E4 (apoE4), thereby attenuating or reversing the pathology of AD.

In another embodiment the present invention relates to a compound which is a functional activator of ATP binding cassette protein type 1 (ABCA1), for use in treating Alzheimer's Disease (AD), wherein activation of ABCA1 results in lipidation of apolipoprotein E4 (apoE4), thereby attenuating or reversing the pathology of AD. According to some embodiments, the pharmaceutical compositions of the present invention are suitable for the treatment of Alzheimer's Disease. According to some embodiments, the pharmaceutical compositions of the present invention are for the treatment of Alzheimer's Disease.

In another embodiment, the present invention relates to the use of a compound which is a functional activator of ATP binding cassette protein type 1 (ABCA1), in treating Alzheimer's Disease (AD), wherein activation of ABCA1 results in lipidation of apolipoprotein E4 (apoE4), thereby attenuating or reversing the pathology of AD. The term "functional activator" of ABCA1 refers to a compound that activates or increases the enzymatic activity of ABCA1 and or ABCA1 driven lipid efflux. Functional activation of ABCA1 drives lipidation of apoE4, thus reversing its hypo-lipidated state that is a hallmark of the cognitive and brain pathological defects of AD. In some embodiments, the compound directly increases the enzymatic activity of ABCA1.

As described herein, more than a half of the AD population are apoE4 positive. This population is expected to be sensitive to the compounds of the present invention. Thus, in some embodiments, apoE4 is hypo-lipidated in an AD patient, and administration of the compound reverses the hypo-lipidation of apoE4 and, consequently, the associated brain pathological and cognitive impairment associated with AD.

In one embodiment, treatment of AD comprises attenuating or reversing the pathology of AD. This includes, but is not limited to, reducing accumulation of amyloid β (Aβ) and/or hyperphosphorylated tau tangles in hippocampal neurons, reversing synaptic impairment, improving cognitive function, and any combination thereof. Each possibility representing a separate embodiment of the present invention.

In another embodiment, the present invention relates to a compound used to increase lipidation of hypo-lipidated apolipoprotein E4 (apoE4). Therefore, the present invention provides a pharmaceutical composition comprising a compound as disclosed herein for increasing lipidation of apoE4. According to some embodiments, the compound is a functional activator of ABCA1. According to some embodiments, the pharmaceutical composition further comprises a at least one pharmaceutically acceptable carrier, diluent and/or excipient. Preferably, the compound is brain permeable, i.e., it penetrates the blood-brain-barrier (BBB). In one embodiment, the compound is represented by the structure of formula (I). In one embodiment, the compound is represented by the structure of formula (I-a). In other embodiments, the compound is represented by the structure of formula (IIa). In other embodiments, the compound is represented by the structure of formula (IIb). In other embodiments, the compound is represented by the structure of formula (III). In other embodiments, the compound is represented by the structure of formula (IV). In other embodiments, the compound is represented by the structure of formula (V). In one embodiment, the compound is represented by the structure of any of Compounds A, B, C, D, E, F, G, H, J, K, L, M, N, O, P, Q, R, S, T and U. Each possibility represents a separate embodiment of the present invention.

In another embodiment, the present invention relates to a method of increasing lipidation of hypo-lipidated apolipoprotein E4 (apoE4), comprising the step of contacting said apoE4 with an ATP binding cassette protein type 1 (ABCA1) in the presence of a non-peptidic compound which is a functional activator of ABCA. In some embodiments, the method is performed in-vitro, e.g., in a cell-free medium or in cell culture.

As used herein, the terms "Alzheimer disease", "Alzheimer's disease" and "AD" are used herein interchangeably, and refer to all types and stages of the disease including preclinical and prodromal stages; also known as "dementia of the Alzheimer type". Alzheimer's disease is characterized by memory deficits in its early phase. Later symptoms include impaired judgment, disorientation, confusion, behavior changes, trouble speaking, and motor deficits. Histologically, AD is characterized by beta-amyloid plaques and tangles of protein tau as well as synaptic impairments and neurodegeneration. As contemplated herein, AD is characterized by hypo-lipidation of apoE4.

Alzheimer's disease is further classified by the age subgroup by which it first manifests in subject. Early-onset Alzheimer's Disease (EOAD) affects people younger than age 65, who present with Aβ plaques and neurofibrillary tangle deposits. Over the years, it has been discovered that EOAD results primarily from genetic mutations. A much more prevalent form of AD is late-onset Alzheimer's Disease (LOAD), which affects the older population. Epidemiologic studies exploring the risk factors for LOAD elucidated a large number of associated factors, including important vascular processes. Additionally, a number of genetic associations have been revealed by genome-wide association studies, the most important of which is the apolipoprotein E gene on chromosome 17 (APOE gene, apoE protein) [1]. Other polymorphisms are associated with genes related to inflammation and immune responses, lipid metabolism, and endocytosis/intracellular trafficking, but none of them are as common nor do they have an effect as strong as that of apoE. To date, attempts to modify the molecular processes involved in AD have mainly targeted Aβ and, more recently, tau; nevertheless, these attempts have been mostly unsuccessful. The present invention relates to a new therapeutic approach to treat AD: apoE. Thus, as used herein, the term "Alzheimer's Disease" includes early-onset AD (EOAD) or late-onset AD (LOAD), with each possibility representing a separate embodiment of the present invention.

Atherosclerosis and Inflammation

Atherosclerosis is a progressive disease characterized by the accumulation of lipids and fibrous elements in the large arteries. Cholesterol efflux pathways mediated by ATP-binding cassette (ABC) transporters and high-density lipoprotein (HDL) have been shown to suppress atherosclerosis [19]. ABCA1 is primarily localized in the plasma membrane of cells. ApoA-1 and other apolipoproteins such as apoE can bind directly to cell surface ABCA1. The direct interaction of apoliproproteins with ABCA1 is of key importance to ABCA1-mediated cholesterol efflux. Several studies have implicated ABCA1 in atherosclerosis [19].

Thus, in some embodiments, the present invention relates to a method for treating atherosclerosis, by administering to a subject in need thereof a compound which is a functional activator of ATP binding cassette protein type 1 (ABCA1), wherein activation of ABCA1 results in increased efflux of cholesterol, thereby attenuating or reversing the pathology of atherosclerosis.

In other, embodiments, the present invention relates to a method for treating inflammation, by administering to a subject in need thereof a compound which is a functional activator of ATP binding cassette protein type 1 (ABCA1).

According to some embodiments, the pharmaceutical compositions of the present invention are suitable for the treatment of inflammation. According to some embodiments, the pharmaceutical compositions of the present invention are for the treatment of inflammation. According to some embodiments, the pharmaceutical compositions of the present invention are suitable for the treatment of atherosclerosis. According to some embodiments, the pharmaceutical compositions of the present invention are for the treatment of atherosclerosis.

Cerebral Amyloid Angiopathy (CAA)

Sporadic cerebral amyloid angiopathy (CAA) is a small vessel disease that preferentially involves small cortical and leptomeningeal arteries due to progressive amyloid-β deposition in their walls, CAA occurs frequently in elderly people, and is a common and important cause of symptomatic lobar intracerebral hemorrhage (ICH) [20]. Genetic factors, such as APOE genotype, are important in the pathophysiology of CAA. APOE ε4 appears to enhance vascular amyloid-β deposition in a dose-dependent fashion, while APOE ε2 promotes vasculopathic changes that can lead to vessel rupture. A clinical study in CAA patients with and without intracerebral hemorrhage (ICH), demonstrated that cortical superficial siderosis (CSS, an imaging marker of CAA), and APOE ε2 are related to the hemorrhagic expression of the disease; while APOE ε4 is enriched in nonhemorrhagic CAA [20].

Thus, in some embodiments, the present invention relates to a method for treating cerebral amyloid angiopathy (CAA), by administering to a subject in need thereof a compound which is a functional activator of ATP binding cassette protein type 1 (ABCA1), wherein activation of ABCA1 results in increased lipidation of apolipoprotein E4 (apoE4), thereby treating CAA.

According to some embodiments, the pharmaceutical compositions of the present invention are suitable for the treatment of CAA. According to some embodiments, the pharmaceutical compositions of the present invention are for the treatment of CAA.

Dementia with Lewy Bodies (DLB)

The two neuropathological hallmarks of Alzheimer disease (AD) are the extracellular beta amyloid (Aβ) plaques and the intracellular neurofibrillary tangles, of which the latter is composed of hyperphosphorylated tau protein. Lewy bodies are intraneuronal cytoplasmic inclusions comprising aggregates of α-synuclein and are readily detected by immunohistochemistry using anti-α-synuclein antibodies. In up to 50% of cases of sporadic late-onset AD, comorbid Lewy bodies are found. Lewy bodies are frequent in the setting of moderate-to-severe levels of AD neuropathologic change. The APOE E4 allele is a strong risk factor across the Lewy Body Disease (LBD) spectrum. Recent evidence suggests that apoE might contribute to neurodegeneration through mechanisms unrelated to amyloid processing [21].

In some embodiments, the present invention relates to a method for treating dementia with Lewis Bodies (DLB), by administering to a subject in need thereof a compound which is a functional activator of ATP binding cassette protein type 1 (ABCA1), wherein activation of ABCA1 results in increased lipidation of apolipoprotein E4 (apoE4), thereby attenuating or reversing the pathology of DLB.

According to some embodiments, the pharmaceutical compositions of the present invention are suitable for the treatment of DLB. According to some embodiments, the pharmaceutical compositions of the present invention are for the treatment of DLB.

Taupathy

As mentioned above, APOE4 is a strong genetic risk factor for late-onset Alzheimer disease. ApoE4 increases brain amyloid-β pathology relative to other ApoE isoforms. It has been demonstrated that ApoE affects tau pathogenesis, neuroinflammation, and tau-mediated neurodegeneration independently of amyloid-β pathology [22].

In some embodiments, the present invention relates to a method for treating taupathy, by administering to a subject in need thereof a compound which is a functional activator of ATP binding cassette protein type 1 (ABCA1), wherein activation of ABCA1 results in increased lipidation of apolipoprotein E4 (apoE4), thereby treating taupathy.

According to some embodiments, the pharmaceutical compositions of the present invention are suitable for the treatment of taupathy. According to some embodiments, the pharmaceutical compositions of the present invention are for the treatment of taupathy.

Cerebrovascular Disease and Vascular Dementia

The apolipoprotein E (APOE) ε 4 allele has been consistently found to be frequent in patients with progressive degenerative dementia of the Alzheimer type (DAT). Vascular dementia (VD) may occur as strokes superimposed on presymptomatic DAT. Consistently, it was demonstrated APOE-E4 allele is more frequent in DAT patients than in controls, with VD patients falling in between [23].

In some embodiments, the present invention relates to a method for treating Cerebrovascular disease and/or Vascular Dementia by administering to a subject in need thereof a compound which is a functional activator of ATP binding cassette protein type 1 (ABCA1), wherein activation of ABCA1 results in increased lipidation of apolipoprotein E4 (apoE4), thereby treating Cerebrovascular Disease and/or Vascular Dementia.

According to some embodiments, the pharmaceutical compositions of the present invention are suitable for the treatment of Cerebrovascular Disease and/or Vascular Dementia. According to some embodiments, the pharmaceutical compositions of the present invention are for the treatment of Cerebrovascular Disease and/or Vascular Dementia. According to some embodiments, the pharmaceutical compositions of the present invention are suitable for the treatment of Cerebrovascular Disease. According to some embodiments, the pharmaceutical compositions of the present invention are for the treatment of Cerebrovascular Disease. According to some embodiments, the pharmaceutical compositions of the present invention are suitable for the treatment of Vascular Dementia. According to some embodiments, the pharmaceutical compositions of the present invention are for the treatment of Vascular Dementia.

Multiple Sclerosis

Apolipoprotein E (ApoE) also functions as a ligand in receptor-mediated endocytosis of lipoprotein particles and has been demonstrated to play a role in antigen presentation. Expression of ApoE was elevated in an experimental autoimmune encephalomyelitis (EAE) mouse model of multiple sclerosis. Overall, ApoE promotes clinical EAE, likely by mediation of inflammation localized within the CNS [24].

In some embodiments, the present invention relates to a method for treating multiple sclerosis, by administering to a subject in need thereof a compound which is a functional activator of ATP binding cassette protein type 1 (ABCA1), thereby treating or reducing/attenuating the symptoms of multiple sclerosis.

According to some embodiments, the pharmaceutical compositions of the present invention are suitable for the treatment of multiple sclerosis. According to some embodiments, the pharmaceutical compositions of the present invention are for the treatment of multiple sclerosis.

Traumatic Head Injury

Traumatic brain injury (TBI) is a leading cause of death and disability. Previous studies have investigated the association of apolipoprotein E (APOE) 64 with functional outcome after TBI. APOE ε4 was associated with an increased risk of unfavorable long-term (≥6 months) functional outcome after TBI [25].

In some embodiments, the present invention relates to a method for treating TBI, by administering to a subject in need thereof a compound which is a functional activator of ATP binding cassette protein type 1 (ABCA1), thereby treating or reducing/attenuating the progression of TBI.

According to some embodiments, the pharmaceutical compositions of the present invention are suitable for the treatment of TBI. According to some embodiments, the pharmaceutical compositions of the present invention are for the treatment TBI.

Metabolic Syndrome and Glucose Homeostasis

Hepatic ABCA1 is involved in regulation of very low density lipoprotein (VLDL) production by affecting the apolipoprotein B trafficking and lipidation of VLDL particles. This protein is involved in protecting the function of pancreatic β-cells and insulin secretion by cholesterol homeostasis. Adipose tissue lipolysis is associated with ABCA1 activity. This transporter is involved in controlling obesity and insulin sensitivity by regulating triglyceride (TG) lipolysis and influencing on adiponectin, visfatin, leptin, and GLUT4 genes expression. The ABCA1 of skeletal muscle cells play a role in increasing the glucose uptake by enhancing the Akt phosphorylation and transferring GLUT4 to the plasma membrane. Abnormal status of ABCA1-regulated phenotypes is observed in metabolic syndrome [26]. Additionally, it has been suggested that apoE4 is also a risk factor of metabolic syndrome. [28] In some embodiments, the present invention relates to a method for treating metabolic disorder, by administering to a subject in need thereof a compound which is a functional activator of ATP binding cassette protein type 1 (ABCA1), thereby treating the metabolic disorder and restoring glucose homeostasis.

According to some embodiments, the pharmaceutical compositions of the present invention are suitable for the treatment of metabolic disorder. According to some embodiments, the pharmaceutical compositions of the present invention are for the treatment metabolic disorder.

2) Diseases Associated with ABCA1 Independent of apoE4

These diseases correspond to diseases in which ABCAa1 has been implicated in the pathology with no known involvement of apoE4. Tangier disease is a non-limiting example of this group.

Tangier Disease

Reduced circulating levels of high density lipoprotein cholesterol (HDL-C) are a frequent lipoprotein disorder in coronary heart disease patients and can be caused by either genetic and/or environmental factors. Extremely low serum HDL-C levels occur in patients with Tangier disease (TD), which is caused by mutations in ABCA1. Clinical manifestations are related to the storage of cholesteryl esters in reticuloendothelial tissues and to peripheral neuropathy [27].

In some embodiments, the present invention relates to a method for treating Tangier disease (TD) (both heterozygous and homozygous) by administering to a subject in need thereof a compound which is a functional activator of ATP binding cassette protein type 1 (ABCA1), thereby treating TD.

According to some embodiments, the pharmaceutical compositions of the present invention are suitable for the treatment of TD. According to some embodiments, the pharmaceutical compositions of the present invention are for the treatment TD.

Preferably, the compound used to treat any one or more of the diseases and conditions described above is a low molecular weight compound (i.e., it is not a peptide). Therefore, the present invention provides a pharmaceutical composition comprising a compound as disclosed herein for the treatment of any one or more of the diseases and conditions described above. According to some embodiments, the compound is a functional activator of ABCA1. According to some embodiments, the pharmaceutical composition further comprises at least one pharmaceutically acceptable carrier, diluent and/or excipient. Preferably, the compound is brain permeable, i.e., it penetrates the blood-brain-barrier (BBB). In one embodiment, the compound is represented by the structure of formula (I). In one embodiment, the compound is represented by the structure of formula (I-a). In other embodiments, the compound is represented by the structure of formula (IIa). In other embodiments, the compound is represented by the structure of formula (IIb). In other embodiments, the compound is represented by the structure of formula (III). In other embodiments, the compound is represented by the structure of formula (IV). In other embodiments, the compound is represented by the structure of formula (V). In one embodiment, the compound is represented by the structure of any of Compounds A, B, C, D, E, F, G, H, J, K, L, M, N, O, P, Q, R, S, T and U. Each possibility represents a separate embodiment of the present invention.

The term “treating” and “treatment” as used herein refers to abrogating, inhibiting, slowing or reversing the progression of a disease or condition, ameliorating clinical symptoms of a disease or condition or preventing the appearance of clinical symptoms of a disease or condition. The term “preventing” is defined herein as barring a subject from acquiring a disorder or disease or condition.

As used herein, the term “administering” refers to bringing in contact with the composition of the present invention. Administration can be accomplished to cells or tissue cultures, or to living organisms, for example humans. In one embodiment, the present invention encompasses administering the compositions of the present invention to a human subject.

A “therapeutic” treatment is a treatment administered to a subject who exhibits signs of pathology for the purpose of diminishing or eliminating those signs. A “therapeutically effective amount” is that amount of compound or a composition which is sufficient to provide a beneficial effect to the subject to which the compound or composition is administered.

According to some embodiments, the disease or condition treated by any one of the compounds and/or composition of the present invention is characterized by hypo-lipidation of apolipoprotein E4 (apoE4), wherein activation of ABCA1 increases lipidation of apolipoprotein E4 (apoE4). According to some embodiments, the compound directly increases the enzymatic activity of ABCA1. According to some embodiments, the activation of ABCA1 increases efflux of cholesterol.

According to some embodiments, the present invention provides a pharmaceutical composition comprising a compound as disclosed herein and a pharmaceutically acceptable carrier or excipient for the treatment of a condition related to ABCA1, wherein the compound is represented by the structure of formula (I). According to some embodiments, the present invention provides a pharmaceutical composition comprising a compound as disclosed herein and a pharmaceutically acceptable carrier or excipient for the treatment of any one of the diseases described above, wherein the compound is represented by the structure of formula (I). According to some embodiments, the compound is a functional activator of ABCA1.

Formula (I)

In some embodiments, the compound of the present pharmaceutical compositions, uses and methods is represented by the structure of formula (I):

(I)

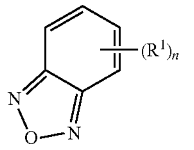

wherein

R' is selected from the group consisting of halogen, nitro ($NO_2$), ($C_1$-$C_6$)-alkyl, $C_2$-$C_8$ alkenyl, $C_2$-$C_8$ alkynyl, cycloalkyl, aryl, heterocyclyl, heteroaryl, ($C_1$-$C_6$)-alkylaryl, ($C_1$-$C_6$)-alkylcycloalkyl, ($C_1$-$C_6$)-alkylheterocyclyl, ($C_1$-$C_6$)-alkylheteroaryl, haloalkyl, hydroxy (OH), ($C_1$-$C_6$)-alkyloxy, aryloxy, thio (SH), ($C_1$-$C_6$)-alkylthio, arylthio, —C(O)R, —C(O)OR, —X—$(CH_2)_t$-G, amino ($NH_2$), —NRR', —C(O)NRR', —S(O)NRR' and —$S(O)_2$NRR';

R and R' are each independently H, ($C_1$-$C_6$)-alkyl, or an aryl, or R and R' together with the nitrogen to which they are attached form a heterocyclic ring; and wherein each of said alkyl, cycloalkyl, heterocyclyl, aryl and heteroaryl is optionally substituted;

X is a bond, O, S or NH;

G is an acidic or basic moiety;

t is selected from the group consisting of 0, 1, 2, 3, 4, 5 and 6;

n is selected from the group consisting of 0, 1, 2, 3 and 4;

and salts and solvates thereof.

In some embodiments, the compound of the present pharmaceutical compositions, uses and method is represented by the structure of formula (I), wherein $R^1$ is selected from the group consisting of halogen, nitro ($NO_2$), ($C_1$-$C_6$)-alkyl, $C_2$-$C_8$ alkenyl, $C_2$-$C_8$ alkynyl, cycloalkyl, aryl, heterocyclyl, heteroaryl, ($C_1$-$C_6$)-alkylaryl, ($C_1$-$C_6$)-alkylcycloalkyl, ($C_1$-$C_6$)-alkylheterocyclyl, ($C_1$-$C_6$)-alkylheteroaryl, haloalkyl, hydroxy (OH), ($C_1$-$C_6$)-alkyloxy, aryloxy, thio (SH), ($C_1$-$C_6$)-alkylthio, arylthio, —C(O)R, —C(O)OR, —X—$(CH_2)_t$-G, amino ($NH_2$), —NRR', —C(O)NRR', —S(O)NRR' and —$S(O)_2$NRR';

R and R' are each independently H, ($C_1$-$C_6$)-alkyl, or an aryl, or R and R' together with the nitrogen to which they are attached form a heterocyclic ring; and wherein each of said alkyl, cycloalkyl, heterocyclyl, aryl and heteroaryl is optionally substituted by a halogen, an alkyl, a hydroxyalkyl or a haloalkyl;

X is a bond, O, S or NH;

G is selected from the group consisting of: $CO_2$H, OH, halogen, $CO_2$—$C_{1-4}$ alkyl, thiocarboxylic acid, dithiocarboxylic acid, sulfonic acid, sulfinic acid, phosphonic acid, and phosphate, an amine, an alkylamine and an arylamine;

t is selected from the group consisting of 0, 1, 2, 3, 4, 5 and 6;

n is selected from the group consisting of 1, 2, 3 and 4; and salts and solvates thereof.

According to some embodiments, the compound is of a pharmaceutical grade purity. According to some embodiments, n is 2 or 3. According to some embodiments, n is 2. According to some embodiments, the compound is a compound having a molecular weight of no more than 600 gr/mol, no more than 500 gr/mol, no more than 450 gr/mol, no more than 400 gr/mol, no more than 350 gr/mol, no more than 325 gr/mol, or no more than 300 gr/mol.

Currently preferred structures have a R' moiety comprised of a 5-7 membered heterocyclic moiety containing at least one N and optionally additional heteroatoms selected from the group consisting of O and S, preferably wherein the N is directly bonded to the aromatic ring of formula (I).

Other currently preferred structures have an $R^1$ group comprised of a group —X—$(CH_2)_t$-G wherein G is an acidic or basic moiety, and X is a bond, O, S or NH; and comprising 3-6 carbon atoms. The acidic moiety G may be any organic or inorganic acidic moiety such as, e.g., carboxylic acid (COOH), thiocarboxylic acid, dithiocarboxylic acid, sulfonic acid, sulfinic acid, phosphonic acid, phosphate, or salts thereof; or any organic or inorganic moiety such as, e.g., amine, alkylamine and arylamine. A currently preferred acidic moiety is carboxylic acid (COOH).

According to some embodiments, at least one $R^1$ group is nitro. According to some embodiments, one $R^1$ group is nitro.

In some embodiments of formula (I), n is 1, 2 or 3, and R' is independently at each occurrence selected from the group consisting of halogen, nitro ($NO_2$), —X—$(CH_2)_t$—C(O)OH and a 5 or 6-membered heterocyclyl or heteroaryl containing one or more heteroatoms selected from the group consisting of O, N and S. In a currently preferred embodiment, R' is a 6-membered group containing a nitrogen atom. In another currently preferred embodiment, the heterocyclic group is connected to the benzo[c][1,2,5]oxadiazole ring through a nitrogen atom.

In some embodiments, n is 2, and $R^1$ is $NO_2$ at the first occurrence, and a 6-membered heterocyclic ring that is connected through a nitrogen atom at the second occurrence. In one currently preferred embodiment, the $NO_2$ and heterocyclic group are para to each other (i.e., they are separated by two carbon atoms). In another currently preferred embodiment, the $NO_2$ and heterocyclic group are ortho to each other (i.e., on adjacent carbon atoms). In some embodiments, the $NO_2$ and heterocyclic group are meta to each other (i.e., they are separated by one carbon atom).

Currently preferred heterocyclic groups are piperazinyl, piperidinyl morpholinyl and pyrrolidinyl:

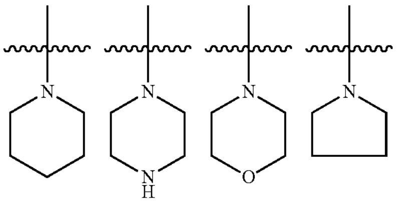

including piperazinyl, piperidinyl, morpholinyl and pyrrolidinyl, which are optionally substituted by at least one alkyl, halogen, haloalkyl and/or hydroxyalkyl. According to some embodiments, the piperazinyl, piperidinyl, morpholinyl and pyrrolidinyl are substituted by at least one alkyl, halogen, haloalkyl and/or hydroxyalkyl. According to some embodiments, the piperazinyl, piperidinyl, morpholinyl and pyrrolidinyl are substituted by at least one alkyl.

In some embodiments, n is 2, and R' is $NO_2$ at the first occurrence, and —X—$(CH_2)_t$-G and the second occurrence. In one currently preferred embodiment, the $NO_2$ and —X—$(CH_2)_t$-G groups are ortho to each other (i.e., on adjacent carbons). In another currently preferred embodiment, the $NO_2$ and —X—$(CH_2)_t$-G are meta to each other (i.e., they are separated by one ring carbon). In another currently preferred embodiment, the $NO_2$ and —X—$(CH_2)_t$-G are para to each other (i.e., they are separated by two ring carbons).

Formula (I-a)

In some embodiments of formula (I), the compound is represented by the structure of formula (I-a):

(I-a)

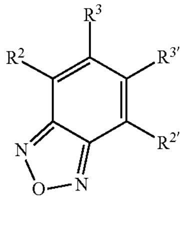

wherein

- $R^2$ and $R^{2'}$ are each independently selected from the group consisting of H, halogen, nitro ($NO_2$), and a 5 or 6-membered heterocyclyl or heteroaryl containing one or more heteroatoms selected from the group consisting of O, N and S; and
- $R^3$ and $R^{3'}$ are each independently selected from the group consisting of H, —X—$(CH_2)_t$-G and halogen;
- X is a bond, O, S or NH;
- G is an acidic or basic moiety;
- t is selected from the group consisting of 0, 1, 2, 3, 4, 5 and 6;

and salts and solvates thereof.

In some embodiments of formula (I), the compound is represented by the structure of formula (I-a), wherein:

- $R^2$ is selected from the group consisting of nitro ($NO_2$) and —NRR';
  - $R^{2'}$ is selected from the group consisting of H, halogen, amino ($NH_2$), and —NRR';
  - R and R' are each independently H, $(C_1\text{-}C_6)$-alkyl, or an aryl, or R and R' together with the nitrogen to which they are attached form a heterocyclic ring; and wherein each of said alkyl, cycloalkyl, heterocyclyl, aryl and heteroaryl is optionally substituted by a halogen, an alkyl, a hydroxyalkyl or a haloalkyl; and
  - $R^3$ and $R^{3'}$ are each independently selected from the group consisting of H, —X—$(CH_2)_t$-G and halogen;

- X is O, S or NH;
- G is $CO_2H$, OH or $CO_2$—$C_{1\text{-}4}$ alkyl;
- t is selected from the group consisting of 0, 1, 2, 3, 4, 5 and 6;

and salts and solvates thereof.

In some particular embodiments of formula (I-a), one of $R^3$ and $R^{3'}$ is H and the other is halogen or X—$(CH_2)_t$—C(O)OH. In other embodiments of formula (I-a), $R^3$ and $R^{3'}$ are each H. In other embodiments of formula (I-a), one or $R^2$ and $R^{2'}$ is H, halogen or $NO_2$ and the other is a halogen or 5-7-membered heterocyclyl or heteroaryl. Non-limiting examples of heterocyclyl or heteroaryl group include unsubstituted or substituted morpholinyl, piperidinyl, piperazinyl, thiazolyl, isothiazolyl, oxazolyl, isoxazolyl, oxadiazolyl, pyrrolyl and furanyl; preferably the heterocyclyl group is selected from the group consisting of morpholinyl, piperazinyl and piperidinyl, each of which may be unsubstituted or substituted.

In another embodiment of formula (I-a), one of $R^2$ and $R^{2'}$ is $NO_2$ and the other is a 6-membered heterocyclic ring that is connected to the benzo[c][1,2,5]oxadiazole ring through a nitrogen atom. In another embodiment of formula (I-a), one of $R^2$ and R' is $NO_2$ and the other is a 5-membered heterocyclic ring that is connected to the benzo[c][1,2,5]oxadiazole ring through a nitrogen atom. In another embodiment of formula (I-a), one of $R^2$ and $R^{2'}$ is $NO_2$ and the other is a 7-membered heterocyclic ring that is connected to the benzo[c][1,2,5]oxadiazole ring through a nitrogen atom. In another embodiment of formula (I-a), one of $R^2$ and $R^{2'}$ is $NO_2$ and the other is a dialkyl amine that is connected to the benzo[c][1,2,5]oxadiazole ring through a nitrogen atom. According to some embodiments, the 5-7 membered heterocyclic ring is unsubstituted. According to some embodiments, the 5-7 membered heterocyclic ring comprises at least one substituent selected from the group consisting of halogen, alkyl, haloalkyl and hydroxyalkyl. According to some embodiments, the 5-7 membered heterocyclic ring comprises at least one substituent selected from the group consisting of alkyl and hydroxyalkyl. According to some embodiments, the 5-7 membered heterocyclic ring comprises at least one alkyl substituent. According to some embodiments, the 5-7 membered heterocyclic ring comprises at least one methyl substituent.

In another embodiment of formula (I-a), one of $R^2$ and $R^{2'}$ is $NO_2$ and the other is a halogen; one of $R^3$ and $R^{3'}$ is —$(CH_2)_t$—C(O)OH and the other is H. The integer t is preferably 1, 2 or 3. According to some embodiments, the halogen is chlorine. In particular embodiments of formula (I) or (I-a), the compound is selected from the group consisting of compounds (C), (F), (G), (H), (J), (K), (L), (Q), (R), (S), (T), (U) and a combination thereof (Table 1). In particular embodiments of formula (I) or (I-a), the compound is selected from the group consisting of compounds (C), (H), and a combination thereof. In particular embodiments of formula (I) or (I-a), the compound is (C). In particular embodiments of formula (I) or (I-a), the compound is (H).

Formulae (IIa) and (IIb)

In some embodiments, the compound of the present pharmaceutical compositions, methods and uses is represented by the structure of formula (IIa) or (IIb):

(IIa)

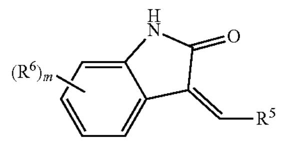

(IIb)

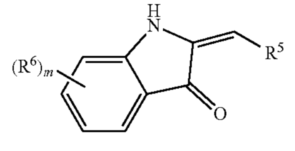

wherein

- $R^5$ is selected from the group consisting of an optionally substituted, optionally fused cycloalkyl, aryl, heterocyclyl and heteroaryl;
- $R^6$ is selected from the group consisting of halogen, nitro ($NO_2$), $(C_1\text{-}C_6)$-alkyl, $C_2\text{-}C_8$ alkenyl, $C_2\text{-}C_8$ alkynyl, cycloalkyl, aryl, heterocyclyl, heteroaryl, $(C_1\text{-}C_6)$-alkylaryl, $(C_1\text{-}C_6)$-alkylcycloalkyl, $(C_1\text{-}C_6)$-alkylheterocyclyl, $(C_1\text{-}C_6)$-alkylheteroaryl, haloalkyl, hydroxy (OH), $(C_1-C_6)$-alkyloxy, aryloxy, thio (SH), $(C_1-C_6)$-alkylthio, arylthio, —C(O)R, —C(O)OR, amino ($NH_2$), —NRR', —C(O)NRR', —S(O)NRR' and —$S(O)_2$NRR';

R and R' are each independently H, $(C_1-C_6)$-alkyl, or an aryl, or R and R' together with the nitrogen to which they are attached form a heterocyclic ring; and wherein each of said alkyl, cycloalkyl, heterocyclyl, aryl and heteroaryl is optionally substituted; and m is selected from the group consisting of 0, 1, 2, 3 and 4;

and salts and solvates thereof.

In some embodiments of formula (IIa) or (IIb), m is 0, and the phenyl of the indolinone moiety is unsubstituted.

In other embodiments of formula (IIa) of (IIb), R is an unsubstituted or substituted, optionally fused cycloalkyl or a 5 or 6-membered heterocyclyl or heteroaryl. In some currently preferred embodiments, $R^5$ is selected from the group consisting of a substituted or unsubstituted morpholinyl, piperidinyl, piperazinyl, thiazolyl, isothiazolyl, oxazolyl, isoxazolyl, pyrrolyl, furanyl and tetradecahydrophenanthrene-2-carboxylic acid, more preferably wherein R is pyrrolyl or tetradecahydrophenanthrene-2-carboxylic acid. Each possibility represents a separate embodiment of the present invention.

In particular embodiments of formula (IIa) or (IIb) the compound is selected from the group consisting of compound (D) and (E) (Table 1).

Formula (III)

In some embodiments, the compound of the present pharmaceutical compositions, methods and uses is represented by the structure of formula (III):

(III)

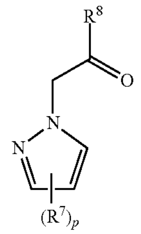

wherein $R^7$ is selected from the group consisting of halogen, nitro ($NO_2$), $(C_1-C_6)$-alkyl, $C_2-C_8$ alkenyl, $C_2-C_8$ alkynyl, cycloalkyl, aryl, heterocyclyl, heteroaryl, $(C_1-C_6)$-alkylaryl, $(C_1-C_6)$-alkylcycloalkyl, $(C_1-C_6)$-alkylheterocyclyl, $(C_1-C_6)$-alkylheteroaryl, haloalkyl, hydroxy (OH), $(C_1-C_6)$-alkyloxy, aryloxy, thio (SH), $(C_1-C_6)$-alkylthio, arylthio, —C(O)R, —C(O)OR, amino ($NH_2$), —NRR', —C(O)NRR', S(O)NRR' and —$S(O)_2$NRR';

R and R' are each independently H, $(C_1-C_6)$-alkyl, or an aryl, or R and R' together with the nitrogen to which they are attached form a heterocyclic ring; and wherein each of said alkyl, cycloalkyl, heterocyclyl, aryl and heteroaryl is optionally substituted;

$R^8$ is selected from the group consisting of an unsubstituted or substituted cycloalkyl, aryl, heterocyclyl and heteroaryl; and p is selected from the group consisting of 0, 1 and 2;

and salts and solvates thereof.

In particular embodiments of formula (III), the compound is represented by the structure of compound (A) (Table 1).

Formula (IV):

In some embodiments, the compound of the present pharmaceutical compositions, methods and uses is represented by the structure of formula (IV):

(IV)

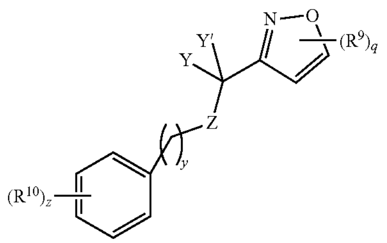

wherein $R^9$ and $R^{10}$ are each independently selected from the group consisting of —C(O)$R^{11}$, halogen, nitro ($NO_2$), $(C_1-C_6)$-alkyl, $C_2-C_8$ alkenyl, $C_2-C_8$ alkynyl, cycloalkyl, aryl, heterocyclyl, heteroaryl, $(C_1-C_6)$-alkylaryl, $(C_1-C_6)$-alkylcycloalkyl, $(C_1-C_6)$-alkylheterocyclyl, $(C_1-C_6)$-alkylheteroaryl, haloalkyl, hydroxy (OH), $(C_1-C_6)$-alkyloxy, aryloxy, thio (SH), $(C_1-C_6)$-alkylthio, arylthio, —C(O)R, —C(O)OR, -amino ($NH_2$), —NRR', —C(O)NRR', —NH—C(O)R, —S(O)NRR' and —$S(O)_2$NRR';

R and R' are each independently H, $(C_1-C_6)$-alkyl, or an aryl, or R and R' together with the nitrogen to which they are attached form a heterocyclic ring; and wherein each of said alkyl, cycloalkyl, heterocyclyl, aryl and heteroaryl is optionally substituted;

$R^{11}$ is selected from the group consisting of $OR^{12}$, $N(R)_2$ and SR wherein $R^{12}$ is selected from the group consisting of $(C_1-C_6)$-alkyl, —$(CH_2)_t$—C(O)$R^{13}$, —$(CH_2)_t$—C(O)$OR^3$ and —$(CH_2)_t$—C(O)NH$R^{13}$ wherein $R^{3'}$ is $(C_1-C_6)$-alkyl or aryl;

Y and Y' are each H or together represent an oxo group (=O);

Z is selected from the group consisting of O, NH and S;

q is selected from the group consisting of 0, 1 and 2;

z and y are each independently selected from the group consisting of 0, 1, 2, 3 and 4;

and salts and solvates thereof.

In particular embodiments of formula (IV) the compound is represented by the structure of compounds (B), (M), (N) or (O) (Table 1).

Formula (V)

In some embodiments, the compound of the present pharmaceutical compositions, methods and uses is represented by the structure of formula (V):

(V)

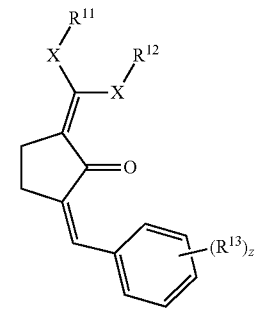

wherein $R^{11}$ and $R^{12}$ are each independently selected from the group consisting of $(C_1-C_6)$-alkyl, $C_2-C_8$ alkenyl, $C_2-C_8$ alkynyl, cycloalkyl, aryl, heterocyclyl and heteroaryl;

$R^{13}$ is selected from the group consisting of halogen, nitro ($NO_2$), $(C_1-C_6)$-alkyl, $C_2-C_8$ alkenyl, $C_2-C_8$ alkynyl, cycloalkyl, aryl, heterocyclyl, heteroaryl, $(C_1-C_6)$-alkylaryl, $(C_1-C_6)$-alkylcycloalkyl, $(C_1-C_6)$-alkylheterocyclyl, $(C_1-C_6)$-alkylheteroaryl, haloalkyl, hydroxy (OH), $(C_1-C_6)$-alkyloxy, aryloxy, thio (SH), $(C_1-C_6)$-alkylthio, arylthio, —C(O)R, —C(O)OR, amino ($NH_2$), —NRR', —C(O)NRR', —NH—C(O)R, —S(O)NRR' and —$S(O)_2$NRR';

R and R' are each independently H, $(C_1-C_6)$-alkyl, or an aryl, or R and R' together with the nitrogen to which they are attached form a heterocyclic ring; and wherein each of said alkyl, cycloalkyl, heterocyclyl, aryl and heteroaryl is optionally substituted; and z is selected from the group consisting of 0, 1, 2, 3, 4 and 5;

and salts and solvates thereof.

In particular embodiments of formula (V) the compound is represented by the structure of compound (P) (Table 1).

Structures of currently preferred compounds are presented in Table 1.

TABLE 1

| Compound number. | Hit # | Structure |
|---|---|---|
| A (formula III) | 3 | 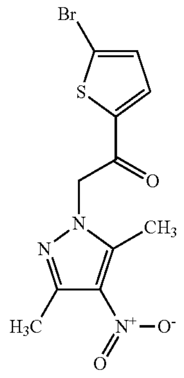 [SMILES: Cc1nn(CC(=O)c2ccc(Br)s2)c(C)c1[N+](=O)[O-]] |
| B (Formula IV) | 4 | 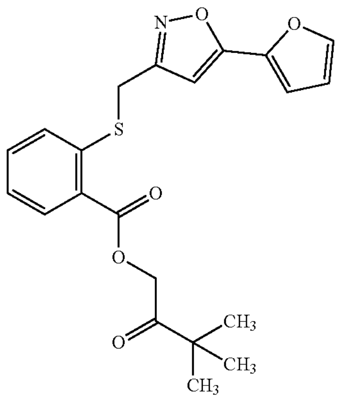 [SMILES: CC(C)(C)C(=O)COC(=O)c1ccccc1SCc1cc(-c2ccco2)on1] |

TABLE 1-continued

| Compound number. | Hit # | Structure |
|---|---|---|
| C (Formula I) | 7 | 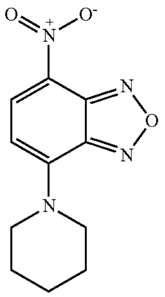 |
| D (Formula II) | 10 | 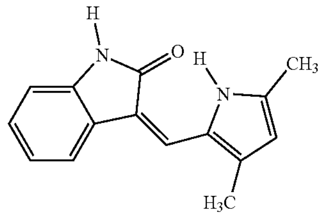 [SMILES: Cc1cc(C)c(/C=C2\C(=O)Nc3ccccc32)[nH]1] |
| E (Formula II) | 12 | 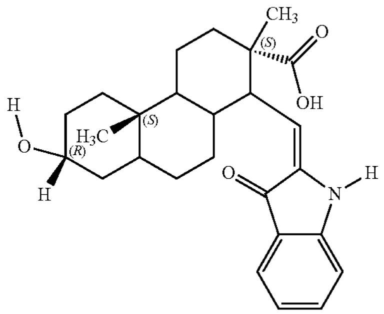 |
| F (Formula I) | 99 | 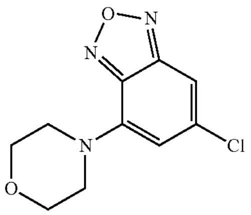 [SMILES: Clc1cc(N2CCOCC2)c2nonc2c1] |
| G (Formula I) | 303 | 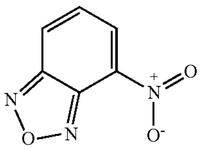 |
| H (Formula I) | N1 | 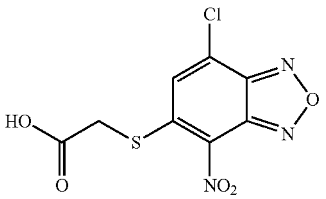 [SMILES: O=C(O)CSc1cc(Cl)c2nonc2c1[N+](=O)[O-]] |

TABLE 1-continued

| Compound number. | Hit # | Structure |
|---|---|---|
| J (Formula I) | | 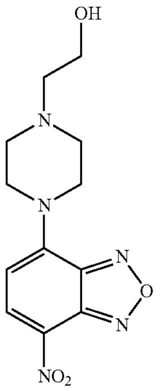 [SMILES: O=[N+]([O-])c1ccc(N2CCN(CCO)CC2)c2nonc12] |
| K (Formula I) | N3 | 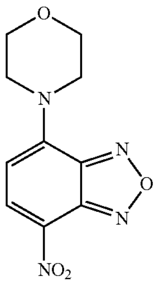 [SMILES: O=[N+]([O-])c1ccc(N2CCOCC2)c2nonc12] |
| L (Formula I) | | 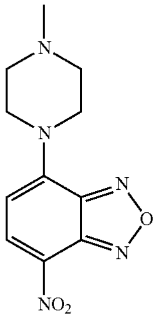 [SMILES: CN1CCN(c2ccc([N+](=O)[O-])c3nonc23)CC1] |
| M (Formula IV) | N2 | 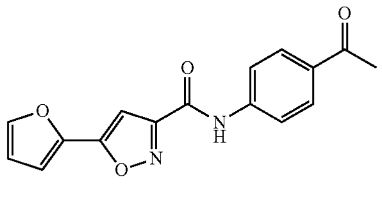 [SMILES: CC(=O)c1ccc(NC(=O)c2cc(-c3ccco3)on2)cc1] |
| N (Formula IV) | | 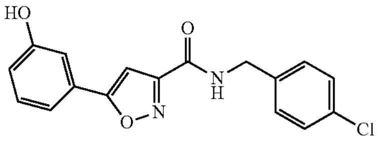 [SMILES: O=C(NCc1ccc(Cl)cc1)c1cc(-c2cccc(O)c2)on1] |
| O (Formula IV) | | 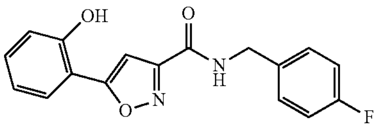 [SMILES: O=C(NCc1ccc(F)cc1)c1cc(-c2ccccc2O)on1] |

TABLE 1-continued

| Compound number. | Hit # | Structure |
|---|---|---|
| P (Formula V) | 14 | 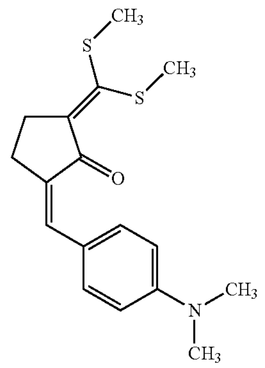 [SMILES: CSC(SC)=C1CC/C(=C/c2ccc(N(C)C)cc2)C1=O] |
| Q (Formula I) | IY-47 | 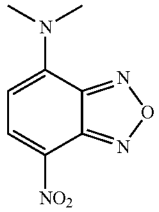 |
| R (Formula I) | IY-54 | 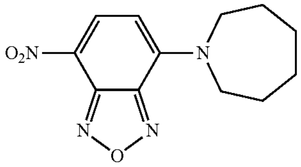 [SMILES: O=[N+]([O-])c1ccc(N2CCCCCC2)c2nonc12] |
| S (Formula I) | IY-56 | 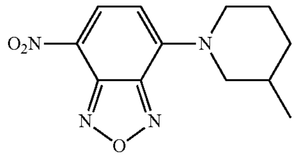 [SMILES: CC1CCCN(c2ccc([N+](=O)[O-])c3nonc23)C1] |
| T (Formula I) | IY-51 | 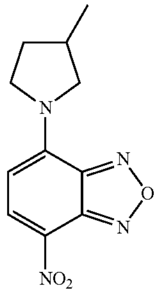 [SMILES: CC1CCN(c2ccc([N+](=O)[O-])c3nonc23)C1] |
| U (Formula I) | IY-57 | 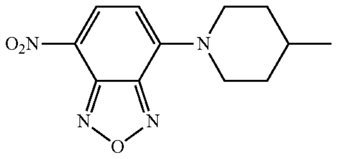 [SMILES: CC1CCN(c2ccc([N+](=O)[O-])c3nonc23)CC1] |

Novel Compounds

The present invention further relates to novel compounds. According to some embodiments, said compounds are ABCA1 functional activators that can reverse the hypolipidation of apoE4 and consequently, the associated brain pathological and cognitive effects of AD.

According to some embodiments, there is provided a compound represented by the structure of formula (I-a), as shown above, wherein $R^2$ is nitro ($NO_2$);

$R^{2'}$ is —NRR';

R and R' together with the nitrogen to which they are attached form a heterocyclic ring, wherein the heterocyclic ring is substituted by at least one $C_{1-4}$ alkyl, and wherein each of said $C_{1-4}$ alkyl and heterocyclic ring is optionally substituted by a halogen;

$R^3$ and $R^{3'}$ are each independently selected from the group consisting of H, $C_{1-4}$ alkyl, COOH, COO— $C_{1-4}$ alkyl and halogen; and salts and solvates thereof.

According to some embodiments, $R^{3'}$ is H. According to some embodiments, $R^3$ is H. According to some embodiments, each of $R^3$ and $R^{3'}$ is H.

According to some embodiments, the substituted heterocyclic ring is selected from the group consisting of methylpiperidine and methylpyrrolidine.

According to some embodiments, the heterocyclic ring is selected from the group consisting of piperidine and pyrrolidine, each of which is substituted by at least one optionally substituted $C_{1-4}$ alkyl. According to some embodiments, the heterocyclic ring is selected from the group consisting of piperidine and pyrrolidine, each of which is substituted by one optionally substituted $C_{1-4}$ alkyl. According to some embodiments, the optionally substituted $C_{1-4}$ alkyl is an optionally substituted $C_{1-3}$ alkyl. According to some embodiments, the optionally substituted $C_{1-4}$ alkyl is an optionally substituted $C_{1-2}$ alkyl. According to some embodiments, the optionally substituted $C_{1-4}$ alkyl is an optionally substituted methyl. According to some embodiments, the $C_{1-4}$ alkyl is unsubstituted. According to some embodiments, the $C_{1-3}$ alkyl is unsubstituted. According to some embodiments, the $C_{1-2}$ alkyl is unsubstituted. According to some embodiments, the $C_{1-4}$ alkyl is $CH_3$.

According to some embodiments, the $C_{1-4}$ alkyl is positioned at the piperidine 3 position or at the pyrrolidine 3 position. According to some embodiments, the $C_{1-4}$ alkyl is positioned at the piperidine 3 position. According to some embodiments, the $C_{1-4}$ alkyl is positioned at the pyrrolidine 3 position. It is to be understood by the skilled in the art that position 1 of a piperidine or pyrrolidine refers to the nitrogen and the subsequent positions are numbered sequentially by the proximity thereto, as shown in the figure below. According to some embodiments, the $C_{1-4}$ alkyl is positioned at the piperidine 2 position or at the pyrrolidine 2 position. According to some embodiments, the $C_{1-4}$ alkyl is positioned at the piperidine 4 position.

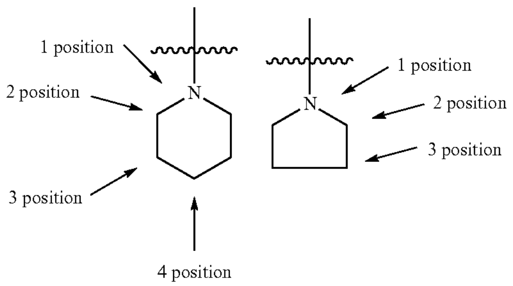

According to some embodiments, the compound is selected from the group consisting of Compound S, Compound T, Compound U, salts and solvates thereof (Table 1). According to some embodiments, the compound is selected from the group consisting of Compound S, Compound T, salts and solvates thereof. According to some embodiments, the compound is selected from the group consisting of Compound S, Compound U, salts and solvates thereof. According to some embodiments, the compound is selected from the group consisting of Compound T, Compound U, salts and solvates thereof. According to some embodiments, the compound is Compound S, a salt or a solvates thereof. According to some embodiments, the compound is Compound T, a salt or a solvates thereof. According to some embodiments, the compound is Compound U, a salt or a solvates thereof.

According to some embodiments, the compound is a compound having a molecular weight of no more than 600 gr/mol, no more than 500 gr/mol, no more than 450 gr/mol, no more than 400 gr/mol, no more than 350 gr/mol, no more than 325 gr/mol, or no more than 300 gr/mol. According to some embodiments, the compound is provided at a pharmaceutical grade. According to some embodiments, the compound is provided at a purity of at least 96%, at least 97%, at least 98%, at least 99%, at least 99.5%, at least 99.8% or at least 99.9%. According to some embodiments, the compound is a functional activator of ABCA1.

In one embodiment the compound is represented by the structure of formula (I). In another embodiment, the compound is represented by the structure of formula (I-a). In another embodiment, the compound is represented by the structure of formula (IIa). In another embodiment, the compound is represented by the structure of formula (IIb). In another embodiment, the compound is represented by the structure of formula (III). In another embodiment, the compound is represented by the structure of formula (IV). In another embodiment, the compound is represented by the structure of formula (V).

Although the compounds of the present invention can be administered alone, it is contemplated that the compounds are administered in pharmaceutical compositions further containing at least one pharmaceutically acceptable carrier or excipient. Thus, in some aspects, the present invention provides a composition comprising a compound according to any one of formulae (I), (I-a), (IIa), (IIb), (III), (IV) or (V) e.g., any one of compounds A-U, and a pharmaceutically acceptable excipient.

As used herein and in the appended claims, the singular forms “a”, “an”, and “the” include plural references unless the context clearly dictates otherwise. Thus, for example, reference to substitution by a substituent includes a plurality of such substituents and combinations thereof. It should be noted that the term “and” or the term “or” are generally employed in its sense including “and/or” unless the context clearly dictates otherwise.

The foregoing examples of the related art and limitations related therewith are intended to be illustrative and not exclusive. Other limitations of the related art will become apparent to those of skill in the art upon a reading of the specification and a study of the figures.

All references cited herein are hereby incorporated by references in their entirety herein.

Example 1: Materials and Methods

Cholesterol efflux assay in HTS. CCF-STTG1 cells were plated in 384-well plates containing 50 µL/well RPMI supplemented with 10% FBS at a density of $5\times10^3$ cells/well, using a Multidrop 384 Reagent Dispenser (Thermo Scientific), and incubated for 48 hr. Cells were washed twice with 50 µl PBS using an EL406 Microplate Washer Dispenser (BioTek, Winooski, VT, USA) before being labeled with 50 μl of 10 μM BODIPY-cholesterol+100 μM cyclodextrin (CD) in RPMI 1640 medium containing 0.2% BSA. The labeling medium was added using in a Washer Dispenser II (GNF, San Diego, CA, USA). Plates were transferred automatically to a Liconic incubator (Mauren Principality of Liechtenstein) and incubated for 24 h. Subsequently, cells were washed twice as described above to remove external cholesterol. Next, 50 μl of the efflux medium was added, which contained recombinant apoE4 at a concentration of 40 μg/ml in transparent RPMI 1640 (no phenol red), again using Washer Dispenser II (GNF, San Diego, CA, USA). The positive control contained the ABCA1 activator, CS-6253 (120 μg/ml) in addition to the acceptor (apoE4). After 7 hr of efflux, the medium was transferred to new plates, using the Bravo Automated Liquid Handling system (Agilent, Santa Clara, CA, USA). Fluorescence polarization (FP) and fluorescence intensity (FI) of the medium were measured in a PheraStar FS plate reader (BMG Labtech, Ortenberg, Germany).

In situ Aβ plaque degradation by apoE3 and apoE4 astrocytes. This assay is based on measurement of the ability of the astrocytes to clear Aβ plaques following their co-incubation with brain sections of 5×FAD mice, which contain Aβ plaques [14, 15]. Accordingly, 20 μm coronal frozen brain sections were prepared from 9-13-month-old 5×FAD mice using cryostat and placed on glass slides, 3-4 consecutive sections in each slide. The slides were kept at −80° C. until used. At the beginning of the experiment, the slices were incubated for 48 hr at 37° C. with apoE3 and apoE4 astrocytes ($10^5$ cells in 100 μl medium per slice) in the presence of 50 μM, or otherwise indicated concentrations, of the HTS hits. The slides were gently placed in round petri dishes with thick wet paper, surrounding the slides. PapPen was used to draw liquid repellent borders of the sections to avoid spillage of coating out of the slides. The slides were gently washed of all containing remains by placing them in PBS for 10 minutes, and were then fixated with 4% PFA for 10 minutes, followed by 0.1% Triton solution for 10 minutes. The slides were then incubated with blocking solution (8% Horse Serum, 0.3% Triton, 1 gr/ml BSA, 0.02% Sodium Azide in PBS) for 30 minutes after which they were immunohistochemically stained with primary anti-PAmyloid (6E10) antibody at a dilution of 1:750 in blocking solution for 1 hr at room temperature. This was then followed by washing (×5 with PBST) and incubation with the secondary antibody (Alexa Fluor® 488 donkey α-mouse IgG, A-21202 at dilution of 1:250 at room temperature for 45 minutes. Nuclei were stained with DAPI (Vektashield, Burlingame, CA; H-1200). Analysis of the Aβ plaque burden was performed as percentage of the area covered in plaques using the ImageJ software.

Microscale thermophoresis (MST) measurements. MST measurements of the binding of the HTS hits to the extracellular domain (ECD) of ABCA1 were performed by two complimentary methods utilizing either fluorescently labeled proteins or the endogenous fluorescence of unlabeled proteins. This was pursued as follows:

(i) MST utilizing labeled proteins: The proteins used in these experiments were Extra-Cellular Domain 1 (ECD1) of ABCA1 and Extra-Cellular Domain 2 (ECD2) which were provided by the manufacturer (Biomatick) at a concentration of 7.1 μM. The buffers of protein samples were exchanged on a desalting PD-10 column to MST labelling buffer (Nanotemper Technologies, NT.115). Each protein was labeled with Alexa Fluor 650 succinimidyl-ester (Thermo Fisher Scientific) in 3-fold excess and then incubated for 1 hr in the dark at room temperature. Excess dye was removed by PD-10 desalting columns. The concentrations of the labeled protein samples solutions were determined by Spectrophotometer (Carey 60) at 280 nm and 650 nm and adjusted to a final concentration 7.1 μM, aliquoted in 30 μl and stored at −80° C. for further use. Protein-compound interactions were analyzed by microscale thermophoresis. The experiments were performed with labelled ECD1 or ECD2 in MST buffer (Nanotemper)+10% DMSO at a concentration of 355 nM. Hits were prepared at the highest concentration soluble in MST buffer (Nanotemper)+10% DMSO. Next, hits were diluted by 2 in 16 consecutive tubes of 10 μl per tube. Then, 10 μl of the protein were added to each tube and centrifuged in 12,000 rpm for 10 minutes. Finally, the samples were loaded to the capillaries and were inserted to the MST machine. Experiments were performed on a microMonolith NT.115 Blue/Red (NanoTemper Technologies) in duplicates. Measurements were performed in standard glass capillaries (NanoTemper Technologies). Measurements were performed at 20%, 40%, 60% and 80% MST power, with hits that did not bind to either ECD1 or 2 serving as negative controls. The ligand concentrations were 1.25 mM as the highest and 38.15 nM as the lowest. For some of the compounds lower concentrations were used due to solubility issues (e.g. usually 0.125 mM as highest and 3.8 nM as lowest). All dissociation constants ($K_D$) were calculated to a binding model assuming a 1:1 stoichiometry per binding partner.

(ii) MST utilizing nonlabelled free proteins: Protein-compound interactions were analyzed by microscale thermophoresis utilizing unlabeled ECD1 and ECD2 in MST buffer (Nanotemper)+10% DMSO in concentration of 355 nM as described above except that the capillaries used were premium treated capillaries (NanoTemper Technologies) and experiments were performed on a Label Free Monolith NT (NanoTemper Technologies). Due to the relatively dilute original stock concentrations of the Analog by Catalog hits #99 (compound F) and #303 (compound G), the highest concentration of these compounds was 250 μM and 500 μM, respectively.

Figure 2:
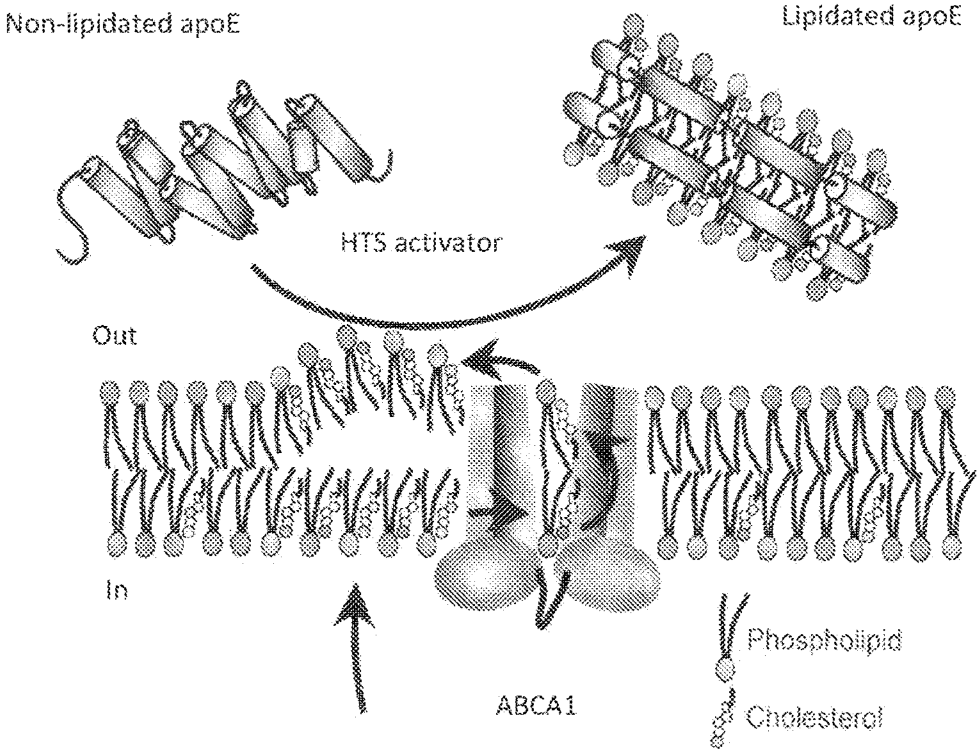
FIG. 2: ABCA1 driven translocation of cholesterol to apoE, used as a basis for an apoE4 lipidation assay.
Figure 3A:
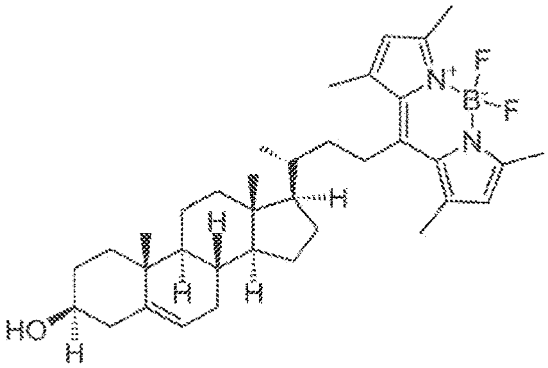
FIGS. 3A-3B: 3A: Structure of BODIPY Cholesterol. 3B: ApoE4 lipidation assay. Human astrocyte derived cells are labeled with fluorescently tagged cholesterol (BODIPY Cholesterol); asoE4 is used as a lipid acceptor in the presence and absence of test compounds; translocation of the fluorescence cholesterol efflux from the cells to the apoE4 is measured by fluorescence polarization.
Figure 3B:
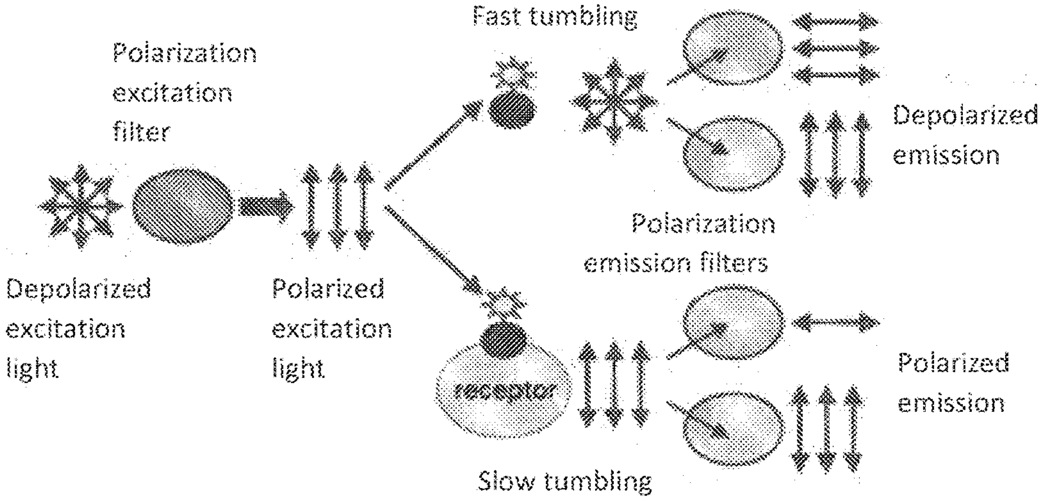

Example 2: Development of the High Throughput Screening (HTS) apoE4 Lipidation Assay The apoE4 lipidation Assay is based on measurements of the ability of astrocytes to translocate fluorescently labelled cholesterol to recombinant non lipidated apoE4 and on the extent to which this effect is enhanced by treatment with each of the screened compounds (FIG. 2, 3). This assay is an adaptation of previous studies of cholesterol translocation from labelled astrocytes to external acceptors such as apoE4 [16], except that in order to differentiate between gene expression related effects and direct biochemical effects of the hits on ABCA1, the incubations of the HTS with the cells was limited to 8 hours. The extent to which the cells secret the labelled cholesterol and transfer it to non-lipidated apoE4 was determined by regular fluorescence as well as by fluorescence polarization microscopy. The latter technique in this context is used due to its sensitivity to particle size which decreases the background signal by differentiating between free and particle bound released cholesterol.

Figure 4:
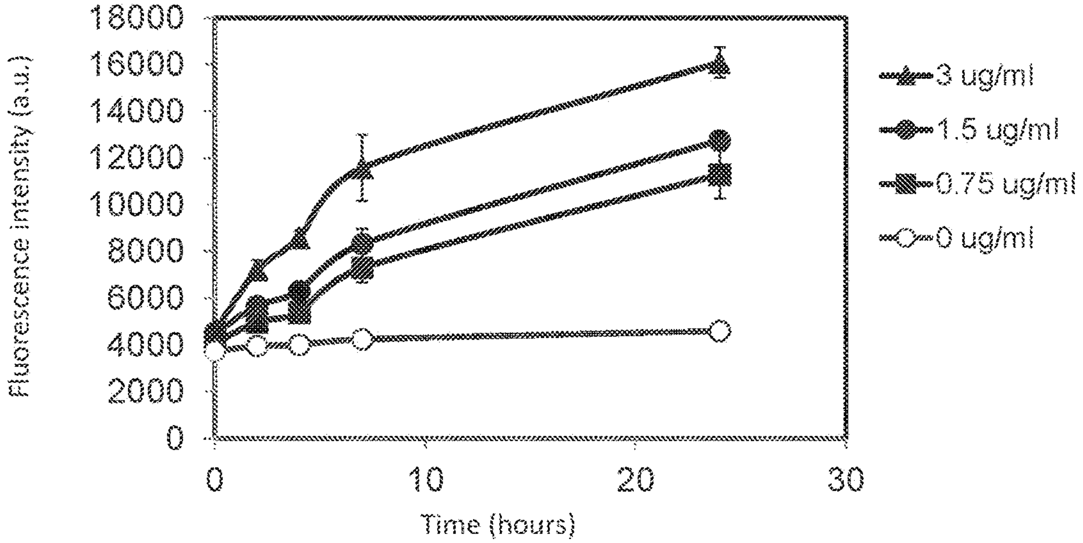
FIG. 4: Translocation to apoE4 of fluorescently labelled cholesterol. Results shown are the time course of translocation of labelled cholesterol from astrocytes to the indicated concentrations of apoE4. Cells were plated at a density of $4\times10^4$ cells/well in growth medium for 48 h and then labeled with 10 μM BODIPY-cholesterol in RPMI 1640 containing 0.2% BSA+100 μM CD for 24 h. Cholesterol efflux was measured in RPMI 1640 containing HDL at a concentration of either 0 μg/ml ("0 ug/ml", empty circles), 0.75 μg/ml ("0.75 ug/ml", full squares), 1.5 μg/ml ("1.5 ug/ml", full circles) or 3 μg/ml ("3 ug/ml", full triangles). Fluorescence intensity (FI) was measured after 0, 2, 4, 7 and 24 h.
Figure 5:
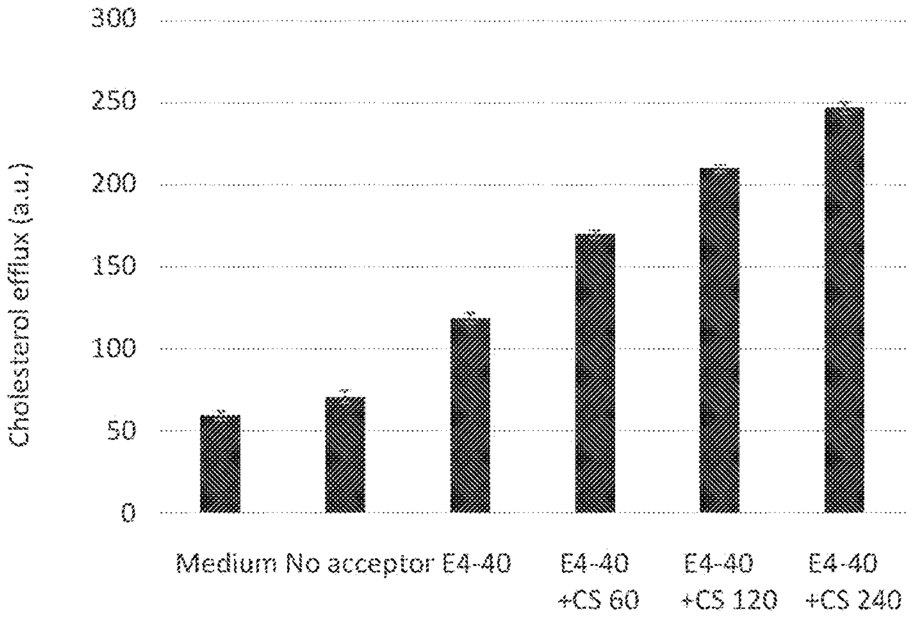
FIG. 5: Positive controls of high throughput screening (HTS) assay utilizing the ABCA Peptide activator CS-6253. Results shown are the additive effect of apoE4 (E4-40) and CS-6253 (CS) on cholesterol translocation to apoE4. Cells were plated at a density of $5\times10^3$ cells/well in growth medium for 48 h and then labeled with 10 μM BODIPY-cholesterol in RPMI 1640 containing 0.2% BSA+100 μM CD for 24 h. Cholesterol efflux was measured in colorless RPMI 1640 containing apoE4 at a concentration of either 10 μg/ml, 40 μg/ml, 80 μg/ml or 160 μg/ml, each of them in addition to CS-6253 at a concentration of 0 μg/ml, 60 μg/ml, 120 μg/ml and 240 μg/ml for 7 h efflux. Two negative controls (left bars) of medium only ("Medium") and medium subjected to the all experimental procedure (cell plating, labeling and efflux) but without addition of acceptor ("No acceptor") were added. BODIPY-cholesterol efflux was measured by fluorescence intensity (FI). The horizontal black line shows the background of the experiment.

The assay was characterized biochemically and it was shown that translocation of labelled cholesterol to apoE4 is time and concentration dependent (FIG. 4) and was increased by the positive control ABCA1 agonistic 26mer peptide CS-6253 [4] (FIG. 5). The assay was used for high throughput screening (HTS) and selection of positive hits.

Figure 6:
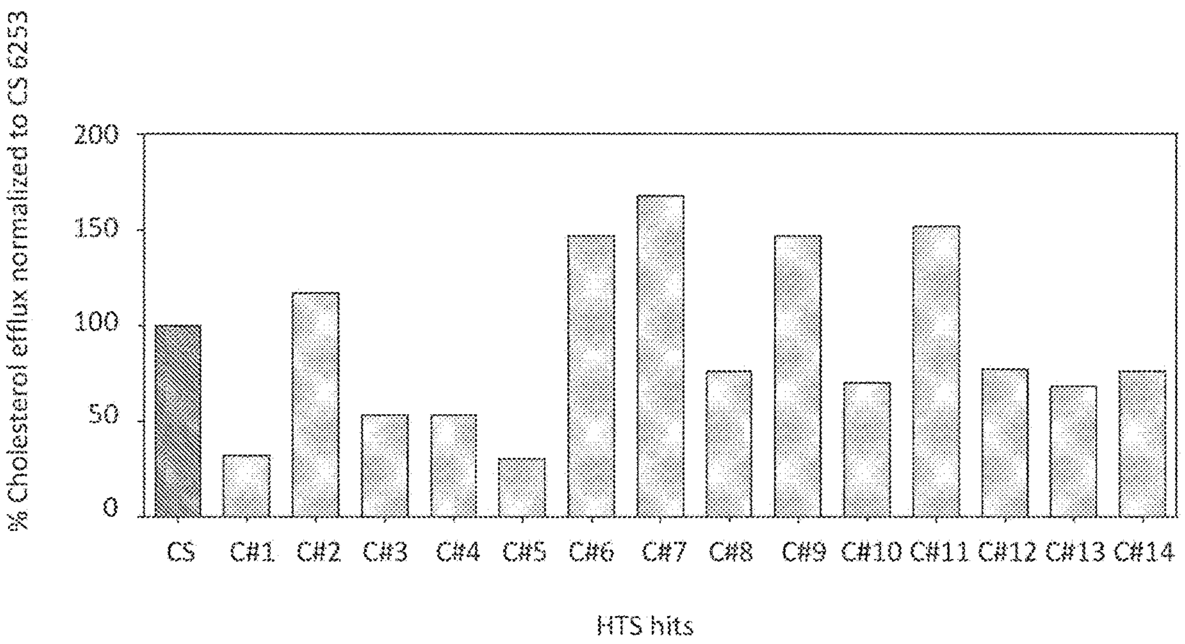
FIG. 6: HTS hits which stimulate cholesterol efflux. Concentration of all test compounds (C #1-14) is 50 μM. Positive control peptide CS-6253 (CS) is 120 μg/ml.

50,000 compounds from commercially available libraries were screened utilizing the double criteria of a signal greater than 3 standard deviations from the mean of all of the screened compounds, and being similar or greater than the apoE4 lipidation driven by the ABCA1 agonistic peptide CS-6253. Additional criteria included the tier drug ability value with tier 1 being best and tier 3 being least suitable, as well as a hydrophobicity value of 2<log P<5 value. This yielded 14 hits, designated Compounds #1-#14 (FIG. 6).

Figure 7:
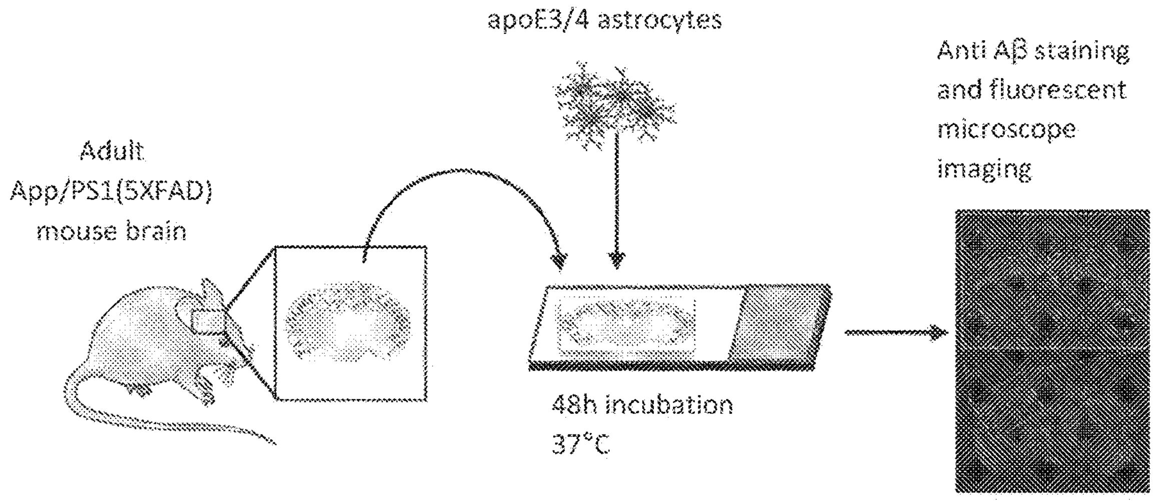
FIG. 7: Schematic representation of assay measuring in situ A$ plaque degradation by apoE3 and apoE4 astrocytes. The assay is designed to measure the ability of astrocytes to digest senile plaques from brain slides of APP mice, which is impaired in apoE4 expressing astrocytes.
Figure 8A:
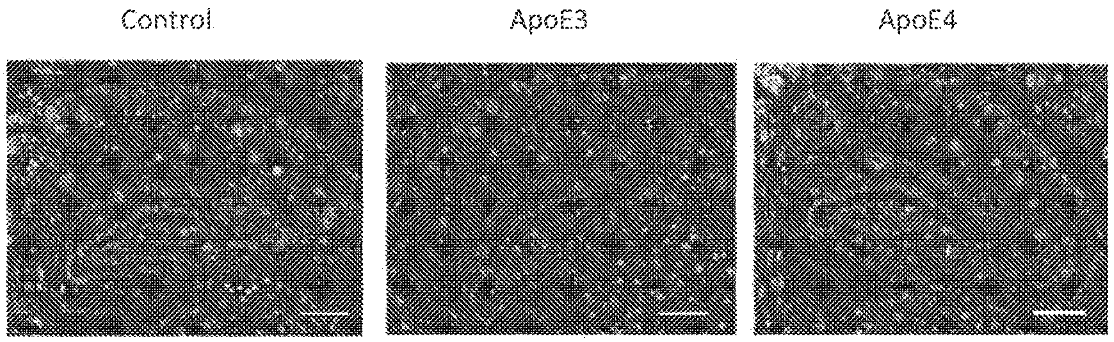
FIGS. 8A-8B: ApoE4 has reduced plaque digestion relative to apoE3 astrocytes in the plaque digestion assay. E4+ HTS represents an exemplary test compound (50 μM) which reverses the apoE4 driven impairment. ApoE3 and apoE4 astrocytes were plated on brain sections of 5×FAD transgenic mice for 48 h. Control sections were treated with medium. Sections were then stained with anti-Aβ antibodies (6E10) to visualize the plaques. 8A: Representative fields of sections treated with apoE4 and apoE3 astrocytes, and of corresponding control medium treated samples. Scale bar=100 μm. 8B: Quantification of total plaque area compared to control (mean±SE; n=11). Results were analyzed using ImageJ software and analyzed using One Way ANOVA for the effects of groups (#, $p<0.01$); and post-hoc Tukey Krammer analysis for comparison of the apoE4 samples to the apoE3 (*, $p<0.05$), and their comparison to the control samples (**, $p<0.01$).
Figure 8B:
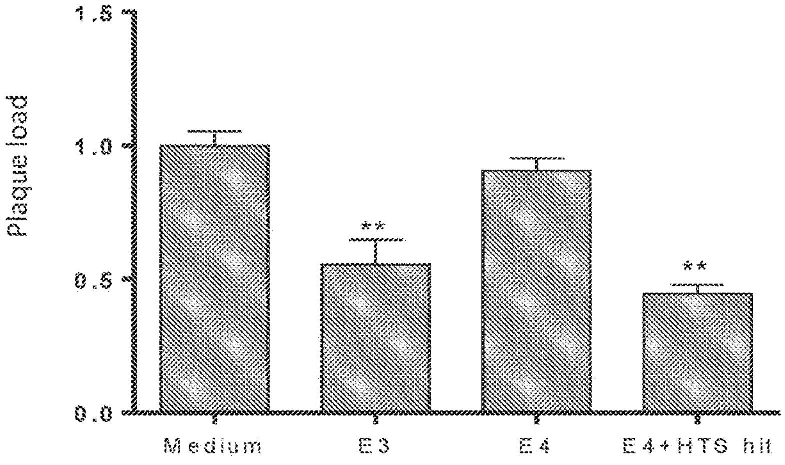
Figure 9:
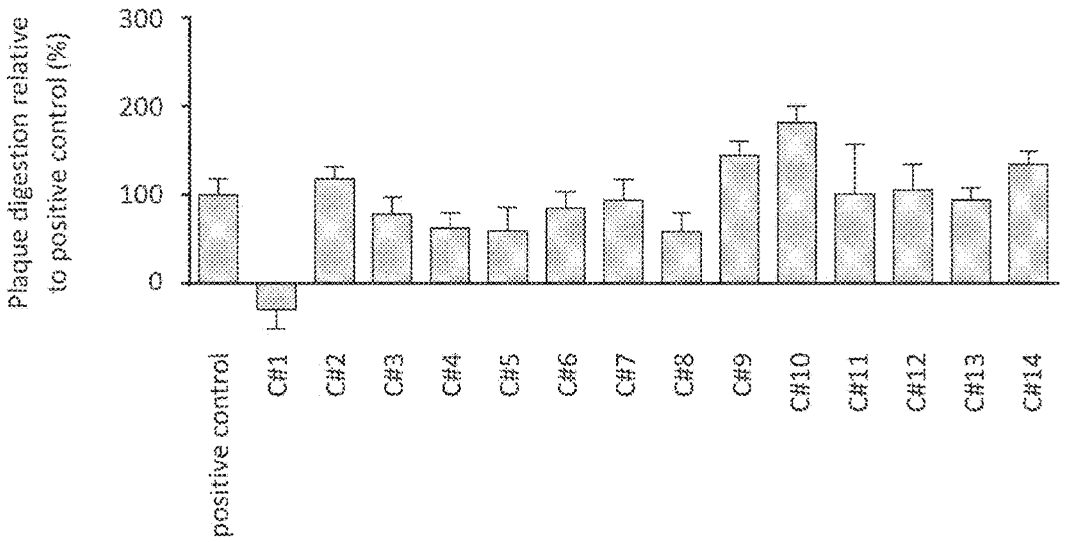
FIG. 9: Activity of test compounds (HTS hits) in the plaque digestion assay. Positive control is CS-6253 (25 μg/ml). Test compound concentration is 50 μM.

Example 3: Characterization of the Hits by an Orthogonal Assay, by Measurements of their Toxicity, by Assessment of the ABCA1 Dependency and the Dose Response of the Effects of the Hits on Cholesterol Efflux The following results were thus obtained:

(i) Orthogonal assay which monitors the extent to which the hits can reverse the impaired ability of apoE4 astrocytes to digest Aβ senile plaques in vitro. The principle of this orthogonal assay is presented in FIGS. 7 & 8 [17], whereas the activity of the HTS hits in this assay is presented in FIG. 9.

Figure 10:
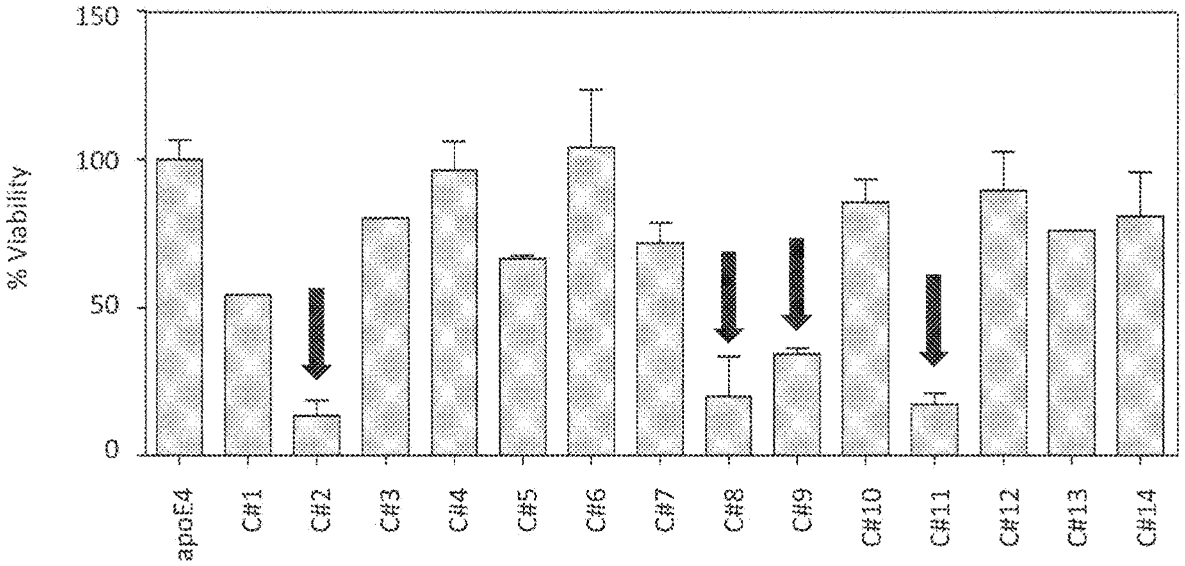
FIG. 10: Effects of test compounds (HTS hits) on cellular viability. Experiments were performed on apoE4 astrocytic cell line [17] in the presence of 50 μM of the indicated compounds. Viability was measured microscopically and by measurements of total cellular protein.

(ii) Measurements of cytotoxicity of the hits. As can be seen in FIG. 10, four of the hits (#2, #8, #9, and #11) were cytotoxic, and were therefore not pursued further.

Figure 11A:
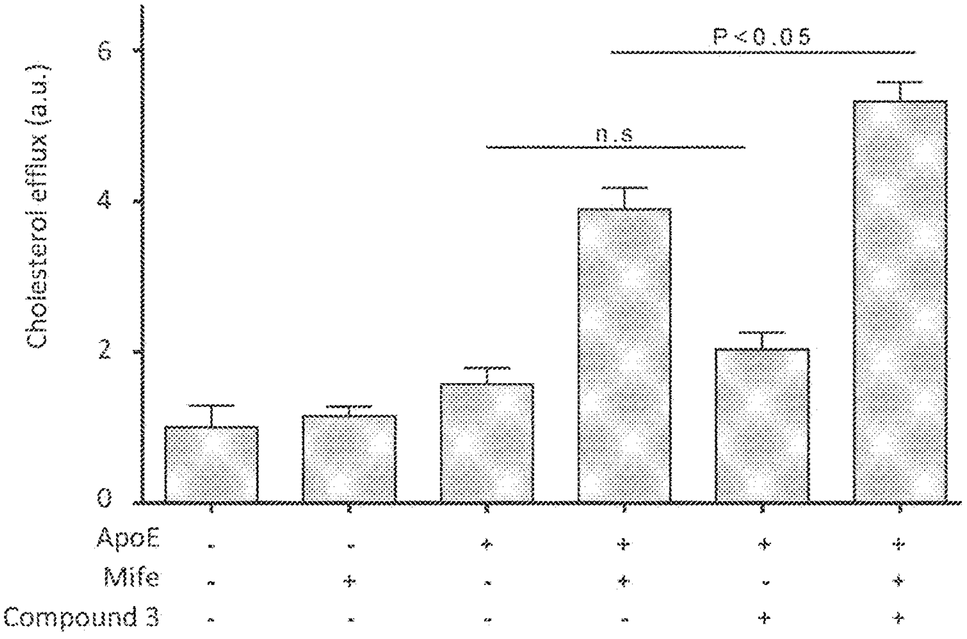
FIGS. 11A-11B: Cholesterol efflux activity of hit #3 (compound A) f BHK cells which either express or do not express ABCA1. Mife=Mifepristone which induces the expression of ABCA1. The experiments were performed on BHK cells in the presence or absence of 50 μM of compound #3 as indicated.
Figure 11B:
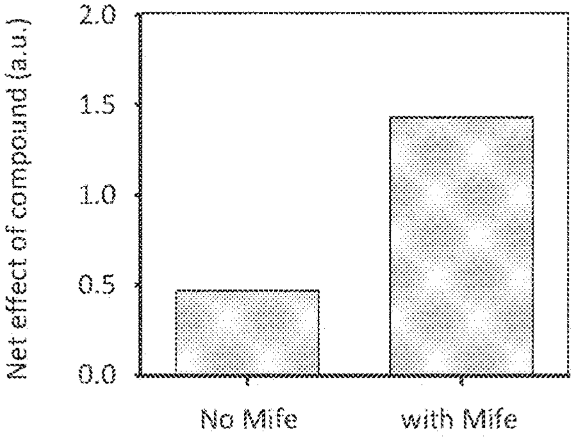
Figure 12A:
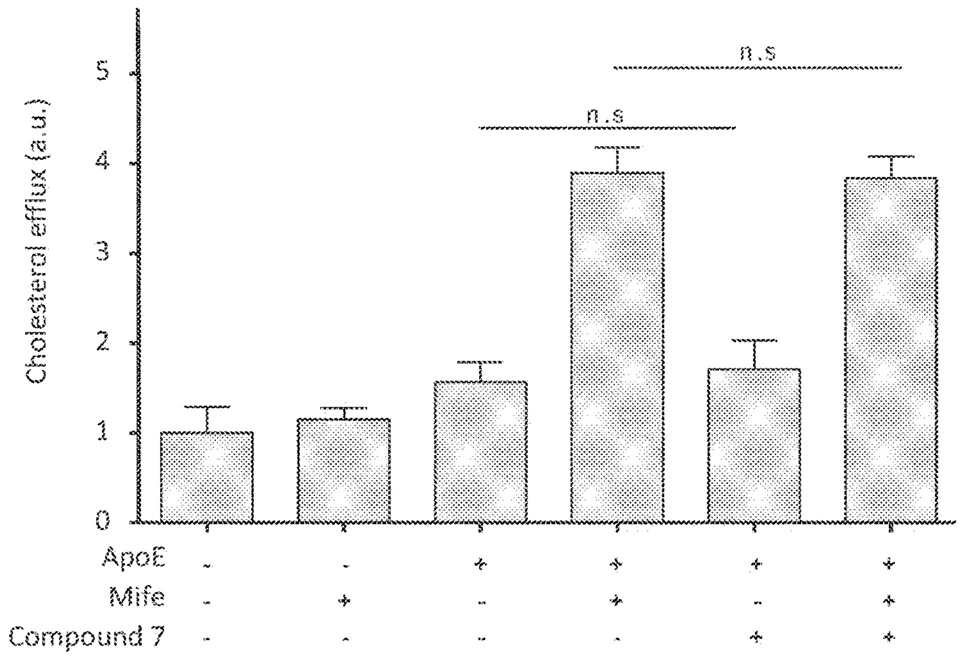
FIGS. 12A-12B: Cholesterol efflux activity of hit #7 (compound B) f BHK cells which either express or do not express ABCA1. Mife=Mifepristone which induces the expression of ABCA1. The experiments were performed on BHK cells in the presence or absence of 50 μM of compound #7 as indicated.
Figure 12B:
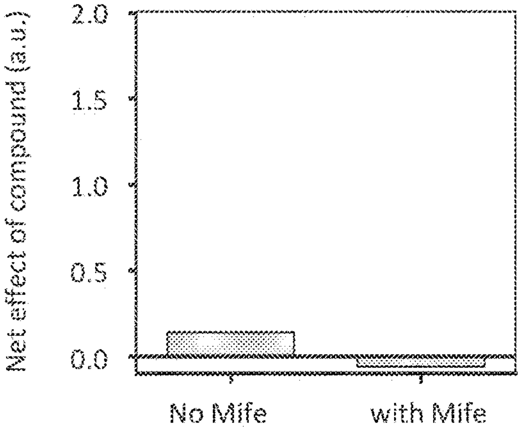
Figure 13A:
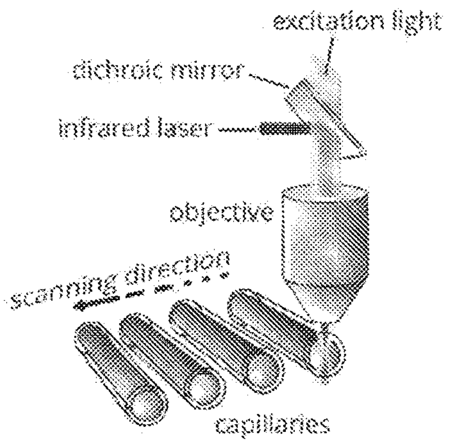
FIGS. 13A-13D: Microscale Thermophoresis (MST) binding assay. Purified extracellular domains 1 and 2 (ECD1 and ECD2) of ABCA1 were used for testing the binding of the indicated compounds to ABCA1. 13A: Schematic presentation of the MST set up. 13B: The MST spectral response following laser activation. 13C: The effects of ligand binding to the protein on its MST response. 13D: Dose response of the effects of ligand binding on the MST response.
Figure 13B:
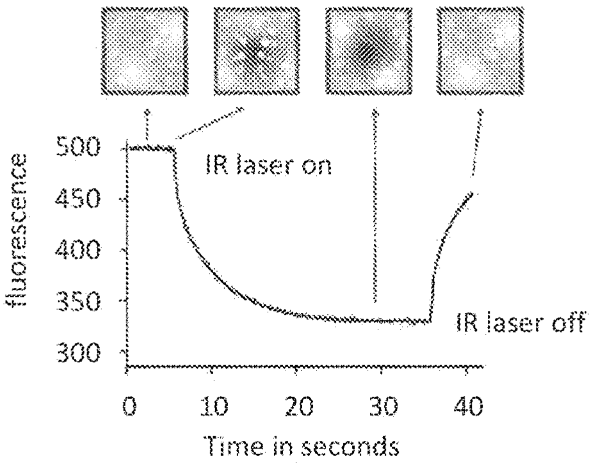
Figure 13C:
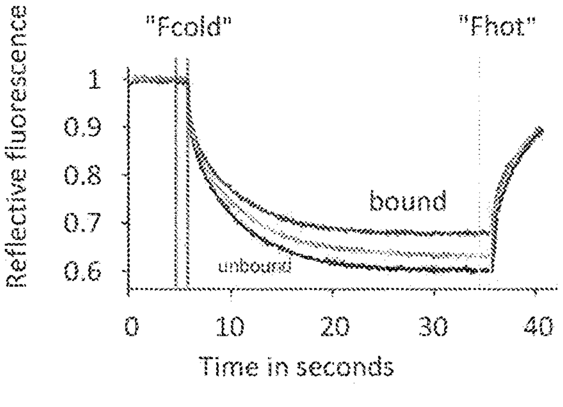
Figure 13D:
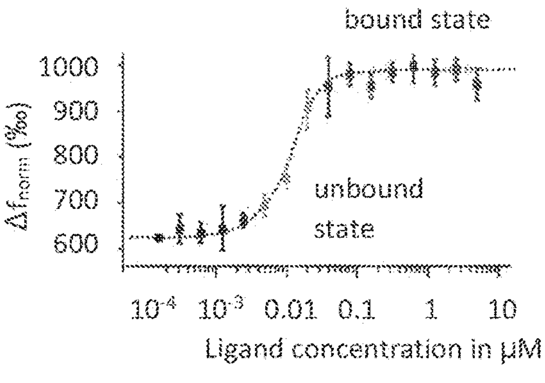
Figure 14A:
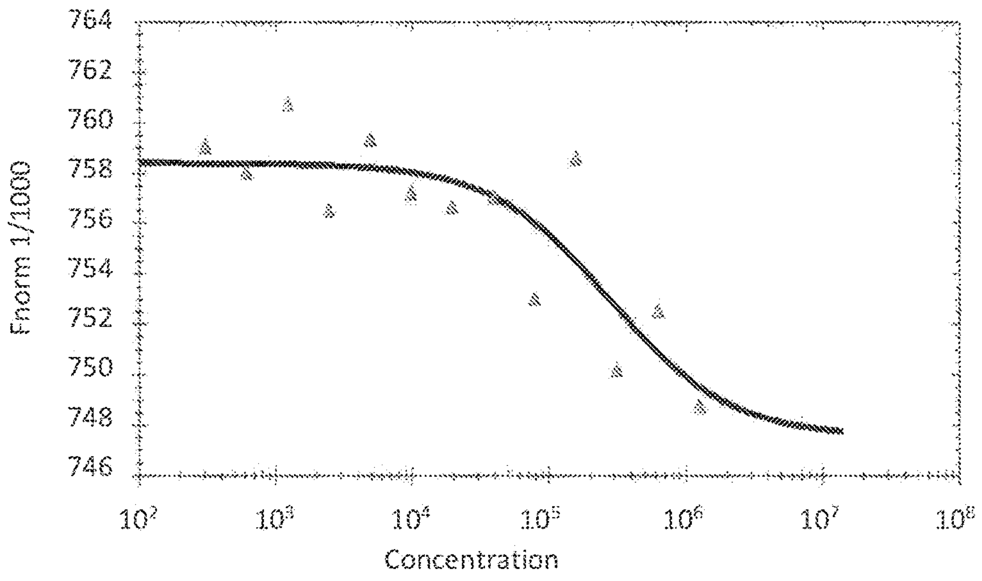
FIGS. 14A-14D: Examples of MST binding results to ECD1 and ECD2 of ABCA1. 14A: Hit #3, binding to ECD1. 14B: Hit #3, binding to ECD2. 14C: Hit #4, binding to ECD1. 14D: Hit #4, binding to ECD2.
Figure 14B:
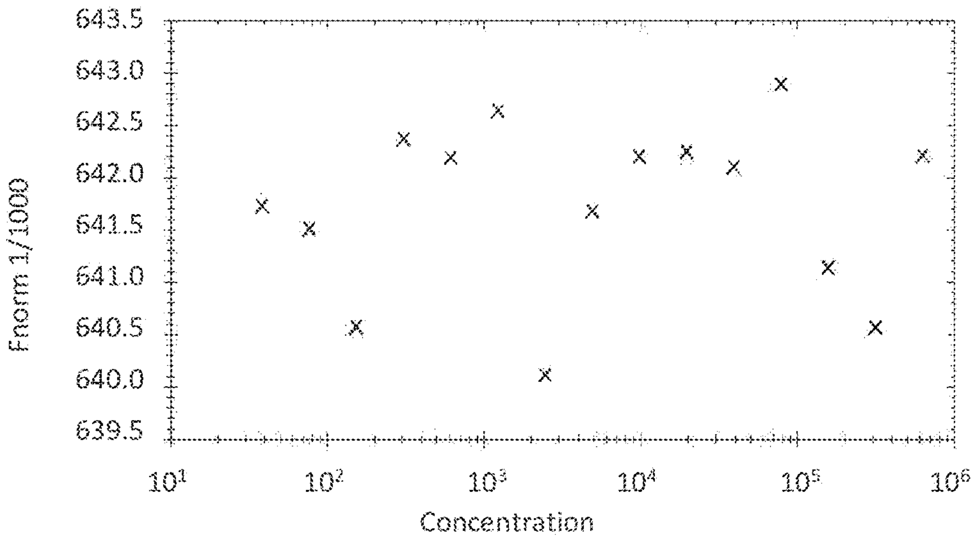
Figure 14C:
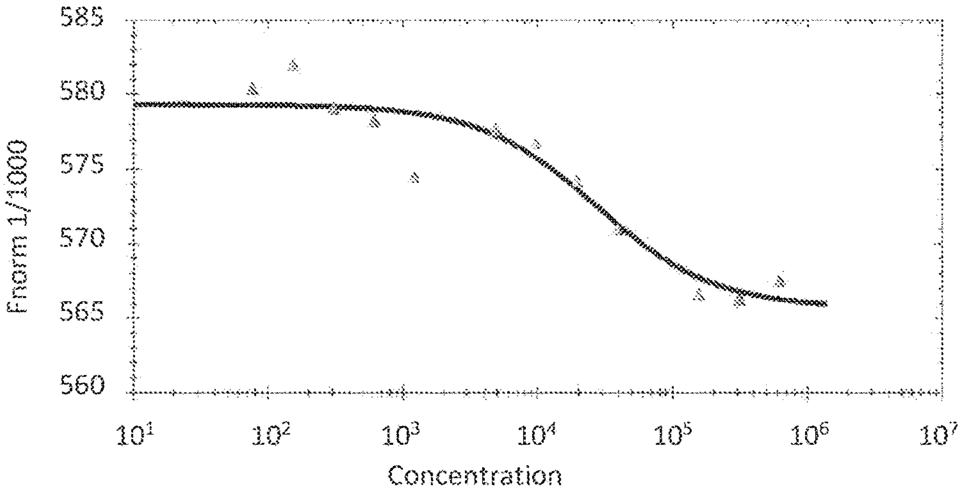
Figure 14D:
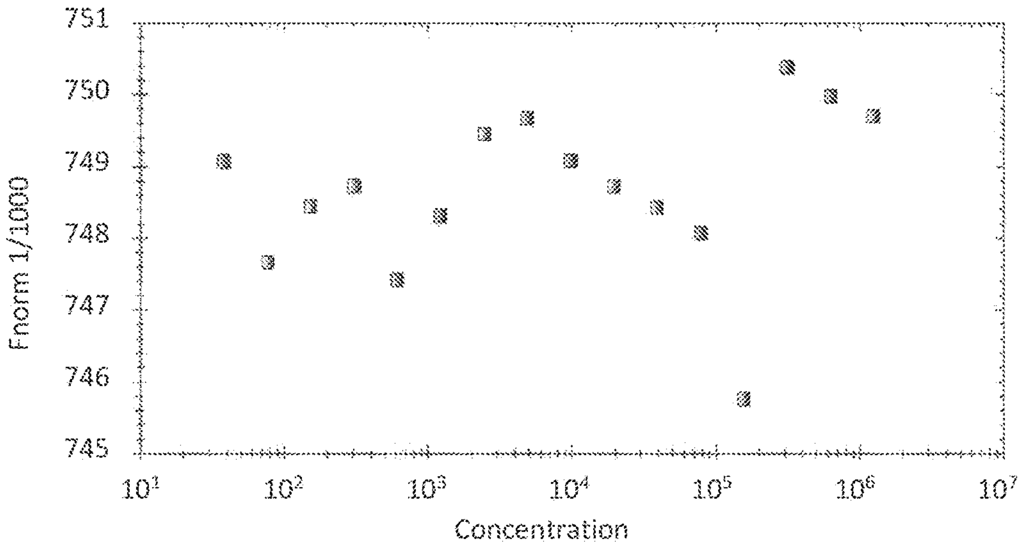

(iii) Assessment of the ABCA1 dependency of the effects of the hits on cholesterol efflux. These experiments investigated the extent to which ABCA1 is indeed the target of the hits. This was performed utilizing BHK (baby hamster kidney) cells with inducible expression of ABCA1 followed by determination of the effects for the presence and absence of ABCA1 on the translocation of cholesterol to apoE4. These experiments, which were thus performed with 4 of the 9 hits (#3 (compound A), #4 (compound B), #7 (compound C), and #10 (compound D)), revealed that the effects of hits #3 and #4 depend on the presence of ABCA1, with this effect being maximal for hit #3, which did not stimulate any lipidation of apoE4 in the absence of ABCA1. The effects of hit #10 did not depend on ABCA1, suggesting that its effects are driven by interactions dependent on the presence of ABCA1, and either apoE4 or cellular membranes. Hit #7, which activates cholesterol efflux from human astrocytes to apoE4, had no effect on cholesterol efflux from ABCA1 expressing BHK cells suggesting that its effects may be cell type specific, namely that they are more active on human astrocytes than in BHK cells. The results obtained with hits #3 and #7 are presented in FIGS. 11 & 12.

(iv) Summary of the results including dose response results is presented in Table 2.

TABLE 2

| # | Tier | Cholesterol efflux $EC_{50}$ (μM) Human Astrocytes | Plaque digestion assay (50 μM) Rodent Astrocytes | Viability Rodent Astrocytes | ABCA1 dependency BHK Cells |
|---|---|---|---|---|---|
| 1 | 1 | >100 | −31% | Normal | N.A. |
| 2 | 1 | >44.8 | 118% | Toxic | N.A. |
| 3 | 1 | >44.8 | 78% | Normal | + |
| 4 | 1 | 28.3 | 62% | Normal | + |
| 5 | 1 | >44.8 | 59% | Normal | N.A. |
| 6 | 1 | 5.31 | 85% | Normal | N.A. |
| 7 | 1 | 8.56 | 93% | Normal | No activity |
| 8 | 2 | 3.53 | 58% | Toxic | N.A. |
| 9 | 2 | >44.8 | 144% | Toxic | N.A. |

TABLE 2-continued

| # | Tier | Cholesterol efflux $EC_{50}$ (μM) Human Astrocytes | Plaque digestion assay (50 μM) Rodent Astrocytes | Viability Rodent Astrocytes | ABCA1 dependency BHK Cells |
|---|---|---|---|---|---|
| 10 | 2 | >44.8 | 182% | Normal | No activity |
| 11 | 2 | 14.1 | 101% | Toxic | N.A. |
| 12 | 2 | >44.8 | 105% | Normal | N.A. |
| 13 | 3 | 31.6 | 94% | Normal | N.A. |
| 14 | 3 | >44.8 | 134% | Normal | N.A. |

*Omitted hits: #2, #8, #9, #11 (toxicity; #1 (low activity))

* +/− ABCA1 (Examined #3, #4, #7, #10)

As can be seen, four of the hits (#2, #8, #9, and #11) were cytotoxic, whereas hit #1 was not effective in the plaque digestion assay. These hits were omitted from further studies, thus leaving 9 hits which stimulate the lipidation of apoE4 with $EC_{50}$=10-50 M; reverse its pathological effects in the orthogonal assay; and are not cytotoxic (Table 2).

Example 4: "Analog by Catalog" (Hit Expansion) Analysis of Compounds Analogous to the HTS Hits The MDLPublic Key and ECSP6 chemical fingerprinting informatics systems and structural similarities/perturbation comparison to tier 1 hits (#3-#7) in over 8 million of catalogued compounds were used by this "analog by catalog" approach to select 62 compounds which were each structurally related to a given HTS. Two additional compounds were identified by this hit expansion methodology.

Example 5: Target Recognition of the HTS Hits: Direct Binding to HTS

These experiments employed the MST ligand binding to protein assay (FIG. 13 and EXAMPLE 1). The experiments were performed with the purified extracellual domains 1 (ECD1) and 2 (ECD2) of ABCA1 [18]. Two complementary MST tests were performed, in which either the proteins were labeled with a fluorescence moiety or the endogenous fluorescence of the unlabeled proteins was monitored). Accordingly, the following experiments were performed:

(i) All 9 original compounds which were positive in the cholesterol efflux and orthogonal tests and were not toxic were tested (see Table 2).

(ii) For Compound #7 which scored positively in the MST test, the "Analog by Catalog" (hit expansion) derived compounds which scored positively in the cholesterol efflux assay were also tested.

Representative binding of compounds #3 and #4 to ECD1 and ECD2 are presented in FIG. 14. As can be seen, these compounds bind saturably to ECD1 but do not bind at all to ECD2. A summary of the MST binding of all the tested compounds is presented in Table 3 which shows that the compounds bind to ECD1 with affinities ranging from 10 to about 300 μM and that importantly none of the compound bind to ECD2.

TABLE 3

| | Binding to ECD1 (Labelled MST) | | Binding to ECD1 (Label free MST) | |
|---|---|---|---|---|
| HTS Hits | Amplitude a.u. | Kd μM | Amplitude a.u. | Kd μM |
| 3 | 10.85 | 278 | 39.96 | 178 |
| 4 | 13.63 | 27 | 16.45 | >350 |
| 5 | 0 | — | 0 | — |
| 6 | 0 | — | 0 | — |
| 7 | 22.05 | NA | No apparent binding | No apparent binding |
| 10 | 0 | — | 40.01 | >350 |
| 12 | 9.05 | 11 | 90.25 | 314 |
| 13 | 0 | — | 0 | — |
| 14 | 0 | — | 0 | — |
| 99 | NA | NA | 24.15 | 59 |
| 303 | NA | NA | 30.59 | 108 |

Summary of Results:

A. HTS Screening and Target Recognition 1. 50,000 compounds from commercial libraries were evaluated in an apoE4 lipidation assay at 50 μM (EXAMPLE 2). Criteria for progression were as follows: a signal greater than 3 standard deviations from the mean of all of the screened compounds, and being similar or greater than the apoE4 lipidation driven by the ABCA1 agonistic peptide CS-6253. This led to identification of 135 hits.
2. Hits were subject to orthogonal test by measurements of their toxicity, assessment of the ABCA1 dependency and the dose response of the effects of the hits on cholesterol efflux (EXAMPLE 3). Criteria for progression was drugability tier designation and log P. This led to identification of 14 hits.
3. Hits were subject to toxicity test, and repeated orthogonal assay, leading to identification of 9 hits (EXAMPLE 3).
4. Target recognition by (a) evaluating whether activity is ABCA1 dependent; and (b) binding to ABCA1 (EXAMPLE 5). This led to identification of 5 hits.

B. HTS Screening and Target Recognition

1. Hit expansion as described in EXAMPLE 4, resulting in 62 compounds structurally similar to hits identified in (A).
2. Target recognition by (a) evaluating whether activity is ABCA dependent; and (b) binding to ABCA1 (EXAMPLE 5). This led to identification of 2 hits.

Conclusions. The paradigms and assays used for the selection of the hits and a summary of their properties are presented in Table 4. The chemical structures are shown in Table 1. Selected compounds are highlighted.

TABLE 4

| # | Tier | Cholesterol efflux $EC_{50}$ (μm) Human Astrocytes | Plaque digestion assay (50 μM) Rodent Astrocytes | Viability Rodent Astrocytes | ABCA1 dependency BHK Cells | Target Recognition (binding to ABCA1) |
|---|---|---|---|---|---|---|
| 1 | 1 | >100 | −31% | Normal | N.A. | N.A. |
| 2 | 1 | >44.8 | 118% | Toxic | N.A. | N.A. |
| 3 | 1 | >44.8 | 78% | Normal | + | + |
| 4 | 1 | 28.3 | 62% | Normal | + | + |
| 5 | 1 | >44.8 | 59% | Normal | N.A. | − |
| 6 | 1 | 5.31 | 85% | Normal | N.A. | − |
| 7 | 1 | 8.56 | 93% | Normal | No activity | + |
| 8 | 2 | 3.53 | 58% | Toxic | N.A. | N.A. |
| 9 | 2 | >44.8 | 144% | Toxic | N.A. | N.A. |
| 10 | 2 | >44.8 | 182% | Normal | No Activity | + |
| 11 | 2 | 14.1 | 101% | Toxic | N.A. | N.A. |
| 12 | 2 | >44.8 | 105% | Normal | N.A. | + |
| 13 | 3 | 31.6 | 94% | Normal | N.A. | − |
| 14 | 3 | >44.8 | 134% | Normal | N.A. | − |
| 99 | | >44.8 | N.A. | N.A. | N.A. | + |
| 303 | | 303 | N.A. | N.A. | N.A. | + |

Example 6: The Effects of #10 and N1 on APOE Lipidation

Figure 15:
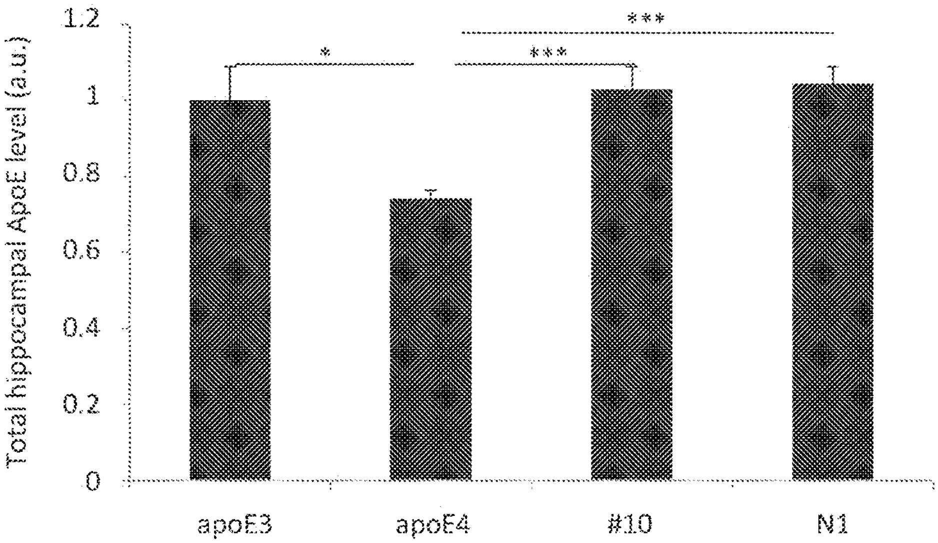
FIG. 15: Total hippocampal ApoE4 levels of mice injected with ACSF and compounds #10 (Compound D) and N1 (Compound H). For reference, total levels of ApoE3 of mice injected with ACSF is also shown. * and *** indicate $p<0.05$ and $p<0.01$, respectively, by Bonferroni correction excel.
Figure 16:
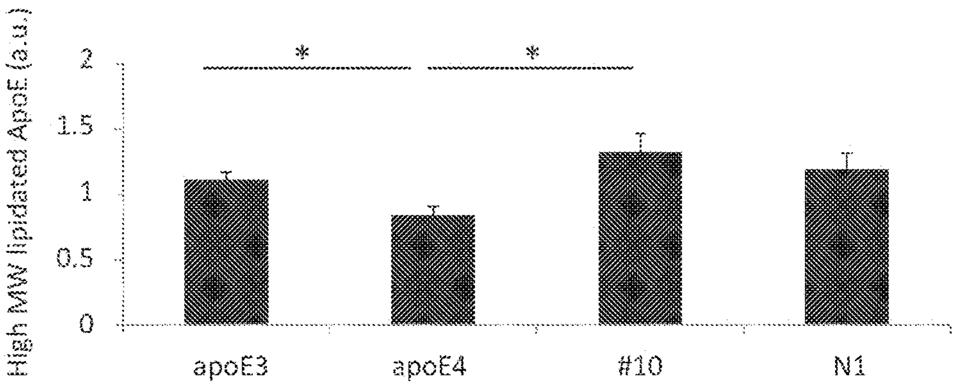
FIG. 16: Levels of high molecular weight lipidated ApoE4 of mice injected with ACSF and compounds #10 (Compound D) and N1 (Compound H). For reference, levels of ApoE3 of mice injected with ACSF is also shown.

These experiments utilized the Alzet osmotic pump to administer labeled compounds #10 and N1 into the ventricles of apoE4 TR mice. The Alzet pumps administered 0.25 μl/hr of the compounds for 11 days. The reagents concentrations were mM and 25 mM for compounds #10 and N1, respectively, reaching estimated concentrations of 200 μM and 250 μM in the CSF. As control groups, apoE3 and apoE4 mice injected with artificial cerebrospinal fluid were used. Four groups, each containing 5 mice were used in the experiments. The total SDS levels in the different groups were measured. While apoE4 has lower levels of SDS than apoE3, FIG. 15 shows that treatment of apoE4 mice with either compound #10 or N1 reversed the effect as evidenced by the increase in SDS levels. Native apoE gels were examined and showed a "smear" like pattern. FIG. 16 depicts the results of the high molecular weight complexes indicating the increase in the apoE4 treated with compounds #10 and N1.

Figure 17A:
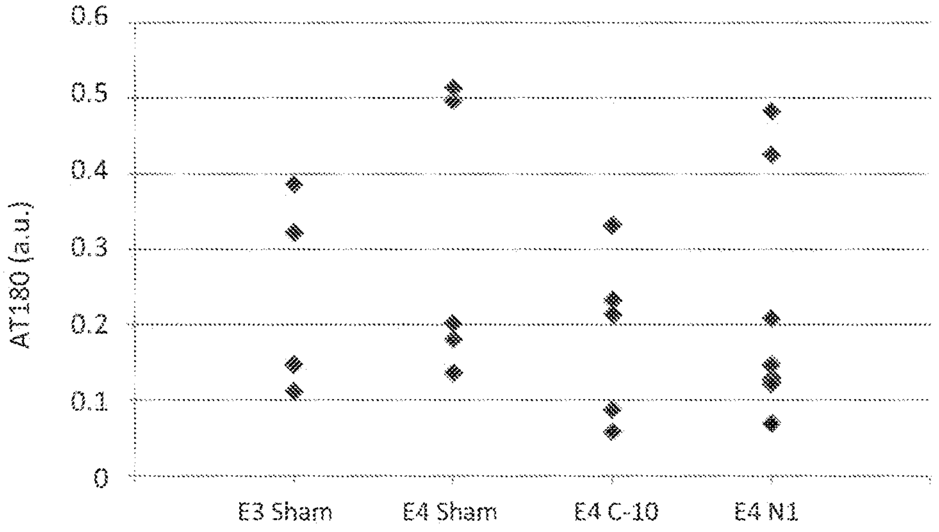
FIGS. 17A-17B: Hippocampal Phosphorylated TAU utilizing monoclonal Ab. AT180 in apoE4 mice injected with ACSF and compounds #10 (Compound D) and N1 (Compound H). For reference, apoE3 mice injected with ACSF is also shown.
Figure 17B:
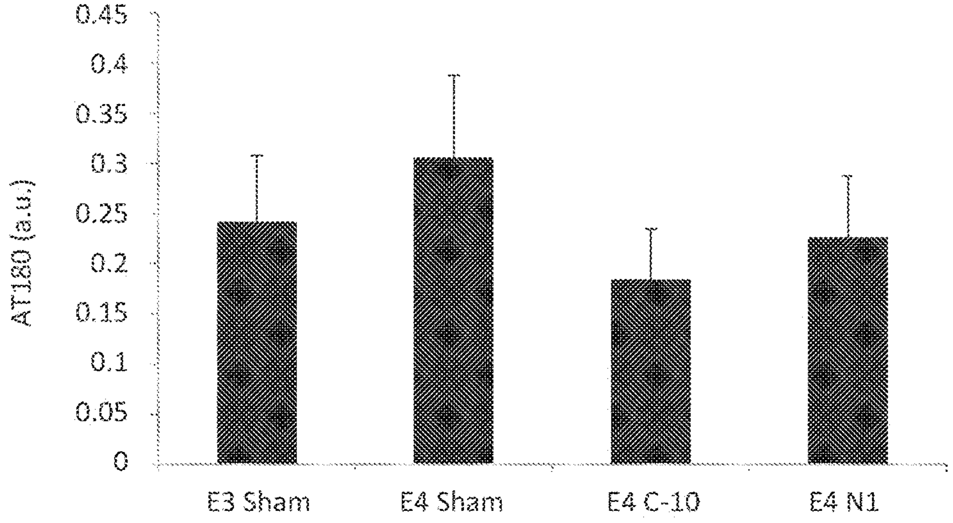

High AT180 corresponds to hyperphosphorylated tau which is pathological. FIG. 17 shows that both compounds #10 and N1 reversed the pathology of apoE4 shams.

Example 7: Chemical Synthesis of Novel Compounds

Compounds IY-51 (compound T), IY-56 (Compound S), and IY-57 (Compound U) are described for the first time herein. The synthesis thereof is based on an aromatic nucleophilic substitution of NBD-chloride with an appropriate amine, as detailed below.

Synthesis of IY-56 (Compound S):

NBD-chloride was reacted with 3-methylpiperidine at room temperature in the presence of triethylamine and dichloromethane, according to the scheme below, to yield IY-56.

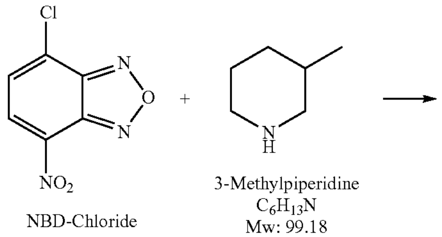

NBD-Chloride

3-Methylpiperidine
$C_6H_{13}N$
Mw: 99.18

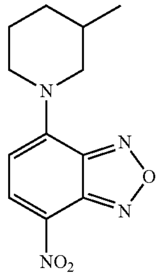

$C_{12}H_{14}N_4O_3$
Mw: 262.27

Synthesis of IY-51 (Compound T):

NBD-chloride was reacted with 3-methylpyrrolidine hydrochloride at room temperature in the presence of triethylamine and dichloromethane, according to the scheme below, to yield IY-51.

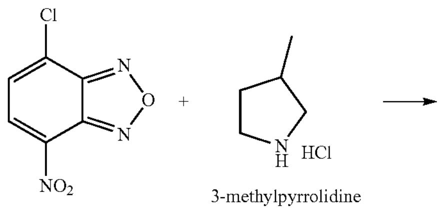

NBD-Chloride 3-methylpyrrolidine
hydrochloride
$C_5H_{12}ClN$
Mw: 121.61

-continued

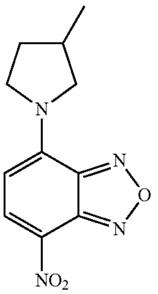

$C_{11}H_{12}N_4O_3$
Mw: 248.24

Synthesis of IY-57 (Compound U):

NBD-chloride was reacted with 4-methylpiperidine at room temperature in the presence of triethylamine and dichloromethane, according to the scheme below, to yield IY-57.

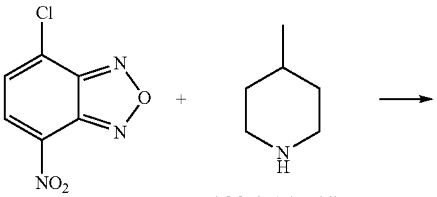

NBD-Chloride

4-Methylpiperidine
$C_6H_{13}N$
Mw: 99.18

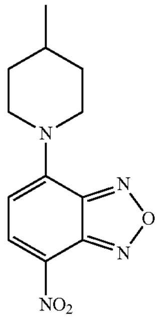

$C_{12}H_{14}N_4O_3$
Mw: 262.27

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

REFERENCES

1. Korczyn A D, Michaelson D M; BMC Med. 2019, 17(1): 64.
2. Giacobini E, Gold G; Nature reviews Neurology 2013, 9: 677-686.
3. Mehta D, Jackson R, Paul G, Shi J, Sabbagh M; Expert Opin Inv Drug 2017, 26: 735-739.
4. Schneider L S, Mangialasche F, Andreasen N, Feldman H, Giacobini E, Jones R, Mantua V, Mecocci P, Pani L, Winblad B, Kivipelto M; J. Internal Medicine 2014, 275: 251-283.

5. Apostolova L G, Risacher S L, Duran T, et al; JAMA Neurol. 2018; 75(3): 328-341.
6. Corder E H, Saunders A M, Strittmatter W J, Schmechel D E, Gaskell P C, Small G W, Roses A D, Haines J L, Pericak-Vance M A; Science 1993, 261: 921-923.
6. Saunders A M, Strittmatter W J, Schmechel D, George-Hyslop P H, Pericak-Vance M A, Joo S H, Rosi B L, Gusella J F, Crapper-MacLachlan D R, et al; Neurology 1993, 43: 1467-1472.
7. Roses A D; Annual Review Med. 1996, 47: 387-400.
8. Yassine H N, Feng Q, Chiang J, Petrosspour L M, Fonteh A N, Chui H C, Harrington M G; J. American Heart Asso. 2016, 5.
9. Hu J, Liu C C, Chen X F, Zhang Y W, Xu H, Bu G; Molecular Neurodegeneration 2015, 10:6.
10. Boehm-Cagan A, Bar R, Liraz O, Bielicki J K, Johansson J O, Michaelson D M; J. Alzheimer's disease 2016, 54: 1219-1233.
11. Boehm-Cagan A, Bar R, Harats D, Shaish A, Levkovitz H, Bielicki J K, Johansson J O, Michaelson D M; PloS one 2016, 11: e0166195.
12. Boehm-Cagan A, Michaelson D M; The J. Neuroscience: The Official J. of the Society for Neuroscience 2014, 34: 7293-7301.
13. Farfara D, Trudler D, Segev-Amzaleg N, Galron R, Stein R, Frenkel D; Annals Neurology 2011, 69: 170-180.
14. Wyss-Coray T, Loike J D, Brionne T C, Lu E, Anankov R, Yan F, Silverstein S C, Husemann J; Nature Medicine 2003, 9: 453-457.
15. Sankaranarayanan S, Kelenr-Weibel G, Llera-Moya M, Philips M S, Aszalos, B F, Bittman R, and Rothblast, G H; J. Lipid Research 2011, 52: 2332-2340.
16. Simonovitch S, Schmukler E, Bespalko A, Iram T, Frenkel D, Holtzman D M, Masliah E, Michaelson D M, Pinkas-Kramarski R J. of Alzheimer's Disease 2016, 51: 915-927.
17. Morikawa M, Fryer J D, Sullivan P M, Christopher E A, Wahrle S E, DeMattos R B, O'Dell M A, Fagan A M, Lashuel H A, Walz T, Asai K, Holtzman D M; Neurobiol Dis. 2005, 19(1-2): 66-76.
18. Hongwu Qian, Xin Zhao, Pingping Cao, Jianlin Lei, Nieng Yan, Xin Gong; Cell 2017, 169:1228-1239.
19. Westerterp M, Bochem A E, Yvan-Chavert L, Murphy A J, Wang N, and Talf; ARCirc Res 2014, 114:157-140.
20. Rannikmae K, Kalaria R N, Greenberg S M, et al; J. Neurol. Neurosurg. Psychiatry 2014, 85(3): 300-305.
21. Tsuang D, Leverenz J B, Lopez O L, et al; JAMA Neurol. 2013, 70(2): 223.
22. Shi Y, Yamada K, Liddelow S A, et al; Nature 2017, 549(7673): 523-527.
23. Treves T A, Bornstein N M, Chapman J, et al; Alzheimer Dis. Assoc. Disord. 1996, 10(4): 189-191; Liu B, Shen Y, Cen L, Tang Y; Dement. Geriatr. Cogn. Disord. 2012, 33(2-3): 96-103.
24. Shin S, Walz K A, Archambault A S, et al; J. Neuroimmunol. 2014, 271(1-2): 8-17; Chapman J, Vinokurov S, Achiron A, et al; Neurology 2001, 56(3): 312-316.
25. Li L, Bao Y, He S, et al; Brain Injury Medicine 2015, 94(46): ε2028.; Kassam I, Gagnon F, Cusimano M D; J. Neurol. Neurosurg. Psychiatry. 2016, 87(4): 433-440.
26. Babashamsi M M, Koukhaloo S Z, Halalkhor S, Salimi A, Babashamsi M; Diabetes Metab Syndr. 2019, 13(2): 1529-1534.
27. Kolovou G D, Mikhailidis D P, Anagnostopoulou K K, Daskalopoulou S S, Cokkinos D V; Curr Med Chem. 2006, 13(7): 771-782.
28. Calderon-Garciduenas and de La Monte J; Alzheimer Disease 2017, 58: 613; Frisadi; Journal Alzheimer Disease 2012, suppl s: S283-304.

What is claimed is:

1. A method for treating a disease or condition related to ATP binding cassette protein type 1 (ABCA1), the method comprising the step of administering to a subject in need thereof a functional activator of ABCA1, wherein the functional activator of ABCA1 is a compound represented by the structure of formula (I-a):

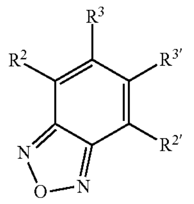

(I-a)

wherein $R^2$ is selected from the group consisting of nitro ($NO_2$) and —NRR';

$R^{2'}$ is selected from the group consisting of H, halogen, and —NRR';

R and R' are each independently H, or ($C_1$-$C_6$)-alkyl, or R and R' together with the nitrogen to which they are attached form a 5-7-membered heterocyclic ring; and wherein each of said alkyl, and heterocyclic ring is optionally substituted by n alkyl or a hydroxyalkyl; and $R^3$ and $R^{3'}$ are each independently selected from the group consisting of H, —X—$(CH_2)_t$-G and halogen;

X is O or S;

G is $CO_2H$, or $CO_2$-$C_{1-4}$ alkyl;

t is selected from the group consisting of 1, 2, and 3;

and salts and solvates thereof; wherein the compound is of a pharmaceutical grade purity;

wherein the disease or condition is selected from the group consisting of Alzheimer's Disease (AD), atherosclerosis, Cerebral amyloid angiopathy (CAA), dementia with Lewy Bodies, taupathy, cerebrovascular disease, multiple sclerosis, vascular dementia, traumatic head injury, metabolic syndrome, glucose homeostasis and Tangier disease (TD).

2. The method according to claim 1, wherein $R^2$ is nitro and $R^{3'}$ is H.

3. The method according to claim 1, wherein $R^{2'}$ is —NRR' and $R^3$ is H.

4. The method according to claim 1, wherein $R^2$ is nitro and $R^{2'}$ is —NRR'.

5. The method according to claim 1, wherein $R^3$, $R^{3'}$ or each one of $R^3$, and $R^{3'}$ is H.

6. The method according to claim 1, wherein the compound is selected from the group consisting of:

-continued

Compound C

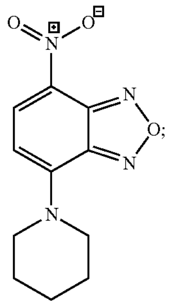

Compound F

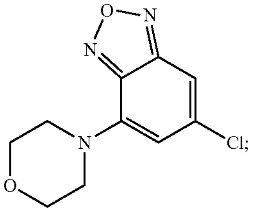

Compound G

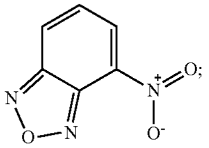

Compound H

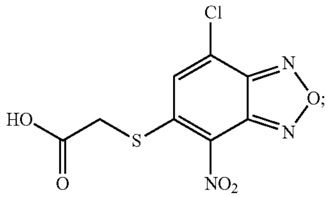

Compound J

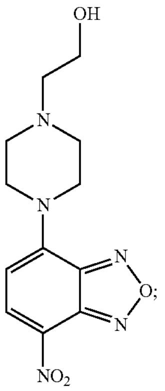

Compound K

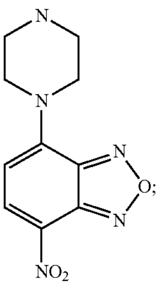

Compound L

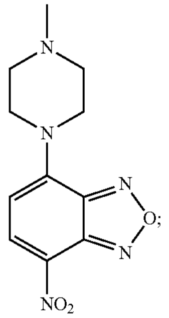

Compound Q

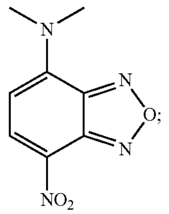

Compound R

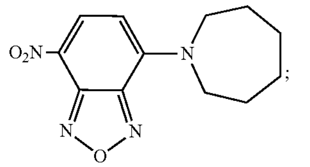

Compound S

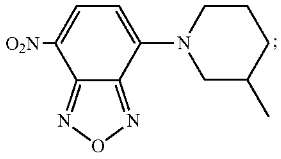

Compound T

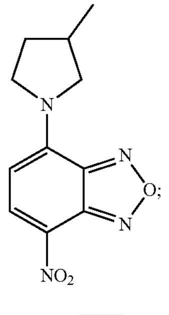

Compound U

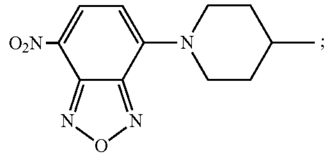

and salts and solvates thereof.

7. The method according to claim 6, wherein the compound is selected from the group consisting of Compound C, Compound H, salts and solvates thereof.

8. The method according to claim 6, wherein the compound is selected from the group consisting of Compound C, Compound F, Compound G, Compound K, Compound Q, Compound R, Compound S, Compound T, Compound U, salts and solvates thereof.

9. The method according to claim 6, wherein the compound is Compound C, a salt or a solvate thereof.

10. The method according to claim 6, wherein the compound is Compound H, a salt or a solvate thereof.

11. The method according to claim 1, wherein the compound directly increases the enzymatic activity of ABCA1.

12. The method according to claim 1, wherein activation of ABCA1 increases efflux of cholesterol.

13. The method according to claim 1, wherein the disease or condition is (a) characterized by hypo-lipidation of apolipoprotein E4 (apoE4); (b) is a disease or condition in which apoE4 has been implicated as a risk factor; or both.

14. The method according to claim 1, wherein the disease or condition is Alzheimer's Disease (AD).

15. The method according to claim 14, wherein treating AD comprises reducing the onset of cognitive impairment associated with AD; delaying the onset of cognitive impairment associated with AD; or both.

16. The method according to claim 14, wherein treating AD comprises attenuating or reversing the pathology of AD by reducing accumulation of amyloid β (Aβ) and/or hyperphosphorylated tau tangles, reversing synaptic impairment, improving cognitive function, or any combination thereof.

* * * * *